US006468771B1

(12) United States Patent
Einerhand et al.

(10) Patent No.: US 6,468,771 B1
(45) Date of Patent: Oct. 22, 2002

(54) ADENO-ASSOCIATED VIRUS AND ADENOVIRUS CHIMERIC RECOMBINANT VIRUSES USEFUL FOR THE INTEGRATION OF FOREIGN GENETIC INFORMATION INTO THE CHROMOSOMAL DNA OF TARGET CELLS

(75) Inventors: Markus Peter Einerhand, Amsterdam; Domenico Valerio, Oegstgeest; Govert Johan Schouten, Leiderdorp, all of (NL)

(73) Assignee: Introgene, Leiden (NL)

( * ) Notice: Subject to any disclaimer, the term of this patent is extended or adjusted under 35 U.S.C. 154(b) by 0 days.

(21) Appl. No.: 09/599,488

(22) Filed: Jun. 23, 2000

Related U.S. Application Data

(63) Continuation of application No. PCT/NL98/00731, filed on Dec. 23, 1998.

(30) Foreign Application Priority Data

Dec. 23, 1997 (EP) .............................................. 97204085

(51) Int. Cl.⁷ .............................................. C12N 15/64
(52) U.S. Cl. ................... 435/91.4; 435/320.1; 435/455; 435/325
(58) Field of Search .......................... 435/172.3, 320.1, 435/325, 455, 91.4; 424/93.2

(56) References Cited

U.S. PATENT DOCUMENTS 6,033,885 A  *  3/2000  Martine

FOREIGN PATENT DOCUMENTS

| WO | WO 93/24641 | | 12/1993 |
| WO | WO 95/23867 | | 9/1995 |
| WO | WO 95/29993 | | 11/1995 |
| WO | WO 96/13598 | * | 5/1996 |
| WO | WO 96/14061 | | 5/1996 |
| WO | WO 97/00326 | | 1/1997 |

OTHER PUBLICATIONS

Hammarskjold et al., Encapsidation of adenoviris 16 DNA is directed by a small DNA sequence at the left end of the genome, 1980, Cell, vol. 20, pp. 787–795.*

Imperiale, Molecular biology of adenovirus gene therapy vectors, 2000, Viral Vectors: Basic Science and Gene Therapy, pp. 119–128.*

Hearing et al., Identification of a repeated sequence element required for efficient encapsidation of the adenovirus type 5 chromosome, 1987, Journal of Virology, pp. 2555–2558.*

Weitzman et al., Recruitment of wild–type and recombinant adeno–associated virus into adenovirus replication centers, 1996, Journal of Virology, pp. 1845–1854.*

Recchia et al., Site–specific integration mediated by a hybrid adenovirus/adeno–associated virus vector, 1999, Proc. Natl. Acad. Sci. USA, vol. 96, pp. 2615–2620.*

Fisher et al., A novel adenovirus–adeno–associated virus hybrid vector that displays efficient rescue and delivery of the AAV genome, 1996, Human Gene Therapy, vol. 7, pp. 2079–2087.*

Verma I. and Somia N. Gene Therapy–rpomises and prospects. 1997, Nature, vol. 389, p. 239–242.*

Somia N. and Verma I. Gene therapy: Trials and Tribulations, Nature Revioews, 2000, vol. 1, p. 94–98.*

Freidmann T. The development of Gene Therapy, Cold Spring Harbor publication, 1999.*

Deonarain M. "Ligand–targeted receptro–mediated vectors for gene delivery"; Exp.Opin.Ther.Patents 8(1):53–69 (1998).*

Crystal R. Trasnfer fo Genes to Humans: early lessons and obstcle to success, 1995, Science vol. 270, p. 404–410.*

Johnston K et al. HSV/AAV Hybrid Amplicon Vectors Extend Trasngene Expression in Human Glioma Cells. 1997, Feb. 10; vol.*, pp 359–370.*

Johnston et al., "HSV/AAV Hybrid Amplicon Vectors Extend Transgene Expression in Human Glioma Cells", *Human Gene Therapy*, 8:359–370, Feb. 10, 1997.

PCT International Search Report, PCT/NL 98/00731, dated Apr. 26, 1999, 2 pages.

* cited by examiner

Primary Examiner—Dave T. Nguyen
Assistant Examiner—Brian Whiteman
(74) Attorney, Agent, or Firm—TraskBritt

(57) ABSTRACT

The present invention provides chimeric viral vectors which have both the capacity to infect host cells efficiently and the capacity to integrate their genomic material into the host cell's genome. The invention provides a chimeric viral vector which comprises a functional packaging signal derived from a first virus and an integration derived from a second virus. Typically, viruses capable of integrating their material into a host cell genome, having additional genetic material introduced therein by recombinant process, do not have much room for insertion of such additional genetic material or are not very well capable of infecting every wanted host cell. Infecting viruses also lack a high insertion capacity or integration into the host cell's genome. The present invention provides integration of large inserts into a host cell's genome at an efficient infection rate by combining the properties of efficiently infecting viruses with efficiently integrating viruses.

14 Claims, 11 Drawing Sheets

AAV-Genome Structure

Identified mRNA's and coding regions

\* ACG translation start of VP2

SEQUENCE LISTING

<160> NUMBER OF SEQ ID NOS: 12

<210> SEQ ID NO 1
<211> LENGTH: 42
<212> TYPE: DNA
<213> ORGANISM: Artificial Sequence

```
<220> FEATURE:
<223> OTHER INFORMATION: Description of Artificial Sequence: primer
<221> NAME/KEY: misc_feature
<222> LOCATION: (1)..(22)
<223> OTHER INFORMATION: A HindIII, a BglII, and a NotI restriction site
      included for cloning purposes

<400> SEQUENCE: 1
ggaagcttag atctgcggcc gcctgactat aataataaaa cg                    42

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: 5' primer
      for Ad y

<400> SEQUENCE: 2
ccaagcttag atcttagtgt ggcggaagtg tgatg                            35

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: 5' primer
      for Ad TR y

<400> SEQUENCE: 3
ccaagcttag atctcatcat caataatata cctta                            35

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: 5' primer
      for D18 AdTR y

<400> SEQUENCE: 4
ccaagcttag atctttattt tggattgaag ccaatatg                         38

<210> SEQ ID NO 5
<211> LENGTH: 51
<212> TYPE: DNA
<213> ORGANISM: Artificial Sequence
<220> FEATURE:
<223> OTHER INFORMATION: Description of Artificial Sequence: upstream
      primer used in amplification of CMV LacZ insert
<221> NAME/KEY: misc_feature
<222> LOCATION: (10)..(29)
<223> OTHER INFORMATION: NotI, ClaI, and SpeI restriction sites
      introduced for cloning purposes

<400> SEQUENCE: 5
gcgtggccag cggccgcatc gatactagtc aggtcgttac ataacttacg g          51

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: downstream
      primer used in the amplification of CMV LacZ
<221> NAME/KEY: misc_feature
<222> LOCATION: (7)..(27)
<223> OTHER INFORMATION: NotI, PmlI, and KpnI restriction sites
      introduced for cloning purposes
```

-continued

```
<400> SEQUENCE: 6
cgccttgcgg ccgccacgtg cggtaccccg ccacactcgc agggtctgca            50

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: palindromic
      sequence encoding an NsiI-site

<400> SEQUENCE: 7
cgatgcatcg                                                        10

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: blunt,
      double stranded oligo linker containing a Pac I site
<221> NAME/KEY: misc_feature
<222> LOCATION: (8)..(15)
<223> OTHER INFORMATION: Pac I site

<400> SEQUENCE: 8
aattgtctta attaaccgct taa                                         23

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence:
      oligonucleotide used to form blunt, double
      stranded oligolinker of SEQ. ID. NO. 8

<400> SEQUENCE: 9
aattgtctta attaaccgc                                              19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence:
      oligonucleotide used to form blunt, double
      stranded oligo linker of SEQ. ID. NO. 8

<400> SEQUENCE: 10
aattgcggtt aattaagac                                              19

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: primer
      ITR-EPH used to amplify the 5' ITR from Ad5

<400> SEQUENCE: 11
cggaattctt aattaagtta acatcatcaa taatatacc                        39

<210> SEQ ID NO 12
<211> LENGTH: 66
<212> TYPE: DNA
<213> ORGANISM: Artificial Sequence
```

```
<220> FEATURE:
<223> OTHER INFORMATION: Description of Artificial Sequence: primer
      ITR-pIX used to amplify the 5' ITR from Ad5

<400> SEQUENCE: 12
acggcgcgcc ttaagccacg cccacacatt tcagtacgta ctagtctacg tcacccgccc      60
cgttcc                                                                 66
```

ADENO-ASSOCIATED VIRUS AND ADENOVIRUS CHIMERIC RECOMBINANT VIRUSES USEFUL FOR THE INTEGRATION OF FOREIGN GENETIC INFORMATION INTO THE CHROMOSOMAL DNA OF TARGET CELLS

RELATED APPLICATIONS

This application is a continuation of pending application PCT/NL98/00731 filed on Dec. 23, 1998, and published under PCT Article 21(2) in English as WO document 99/32647 on Jul. 1, 1999 designating the United States of America, which itself claims priority from European Patent Application 97204085.1 filed on Dec. 23, 1997.

BACKGROUND

1. Field of the Invention

The invention relates to the field of recombinant DNA technology, more in particular to the field of gene therapy. In particular the invention relates to novel methods of delivering DNA to target cells and the subsequent integration of that DNA into the target cell genome.

2. State of the Art

In the field of gene therapy, many different methods have been developed to introduce new genetic information into target cells. Currently, the most efficient means of introducing DNA into target cells is by employing modified viruses, so-called recombinant viral vectors. The most frequently used viral vector systems are based on retroviruses, adenoviruses, herpes viruses or the adeno-associated viruses (AAV). All systems have their specific advantages and disadvantages. Some of the vector systems possess the capacity to integrate their DNA into the host cell genome, whereas others do not. From some vector systems the viral genes can be completely removed from the vector while in other systems this is not yet possible. Some vector systems have very good in vivo delivery properties, while others do not. Some vector types are very easy to produce in large amounts, while others are very difficult to produce.

The present invention combines functional components of two vector systems, thereby combining the favorable properties of both vector systems. The present invention was made during research involving adenovirus and adeno-associated virus. The invention typically provides DNA having a packaging signal which allows it to be encapsidated into virus particles of viruses which allow for encapsidation of large nucleic acids, such as adenovirus particles, which DNA (at least a part thereof) has the capacity to integrate into the host cell genome. The invention also provides for methods to ensure the absence of harmful viral genes from the encapsidated DNA. Absence of viral genes from the vector is the best way to avoid expression of viral gene products in target cells and thus the best way to circumvent immune responses to viral gene products expressed by transduced target cells.

The present invention can convey the above properties onto adenovirus vectors but also to other viruses, such as herpes or polyomaviruses.

The invention will, however, be explained in more detail based on adenovirus and adeno-associated virus vectors. Currently, adenovirus vectors attract a lot of attention and it is expected that the first registered gene therapy medicine will carry the foreign gene into the diseased cells of the patient through adenovirus vector mediated gene transfer. An important problem regarding adenovirus vectors is that they do not integrate into the host cell genome. In rapidly dividing tissue, such as the hemopoietic system, the vector is rapidly lost. Another problem with the current generation of adenovirus vectors is that they are immunogenic. In vivo, vector infected cells are cleared from the body by a potent immune reaction involving both a cellular and a humoral immune component.

For the purpose of gene therapy, adenoviruses carrying deletions have been proposed as suitable vehicles. Gene-transfer vectors derived from adenoviruses (so-called adenoviral vectors) have a number of features that make them particularly useful for gene transfer for such purposes. E.g. the biology of the adenoviruses is characterized in detail, the adenovirus is not associated with severe human pathology, the virus is extremely efficient in introducing its DNA into the host cell, the virus can infect a wide variety of cells and has a broad host-range, the virus can be produced in large quantities with relative ease, and the virus can be rendered replication defective by functional deletion of the early-region 1 (E1) of the viral genome.

During the productive infection cycle, the viral genes are expressed in two phases: the early phase, which is the period up to viral DNA replication, and the late phase, which coincides with the initiation of viral DNA replication. During the early phase only the early gene products, encoded by regions E1, E2, E3 and E4, are expressed, which carry out a number of functions that prepare the cell for synthesis of viral structural proteins (Berk, 1986). During the late phase the late viral gene products are expressed and the early gene products and host cell DNA and protein synthesis are shut off. Consequently, the cell becomes dedicated to the production of viral DNA and of viral structural proteins (Tooze, 1981).

The E1 region of adenovirus is the first region of adenovirus expressed after infection of the target cell. This region consists of two transcriptional units, the E1A and E1B genes, which both are required for oncogenic transformation of primary (embryonal) rodent cultures. The main functions of the E1A gene products are i) to induce quiescent cells to enter the cell cycle and resume cellular DNA synthesis, and ii) to transcriptionally activate the E1B gene and the other early regions (E2, E3, E4). Transfection of primary cells with the E1A gene alone can induce unlimited proliferation (immortalization), but does not result in complete transformation. However, expression of E1A in most cases results in induction of programmed cell death (apoptosis), and only occasionally immortalization is obtained (Jochemsen et al., 1987). Co-expression of the E1B gene is required to prevent induction of apoptosis and for complete morphological transformation to occur. In established immortal cell lines, high level expression of E1A can cause complete transformation in the absence of E1B (Roberts et al., 1985). The E1B encoded proteins assist E1A in redirecting the cellular functions to allow viral replication. The E1B 55 kD and E4 33 kD proteins, which form a complex that is essentially localized in the nucleus, function in inhibiting the synthesis of host proteins and in facilitating the expression of viral genes. Their main influence is to establish selective transport of viral mRNAs from the nucleus to the cytoplasm, concomitantly with the onset of the late phase of infection. The E1B 21 kD protein is important for correct temporal control of the productive infection cycle, thereby preventing premature death of the host cell before the virus life cycle has been completed. Mutant viruses incapable of expressing the E1B 21 kD gene-product exhibit a shortened infection cycle that is accompanied by excessive degradation of host cell chromosomal DNA (deg-phenotype) and in an enhanced cytopathic effect (cyt-phenotype) (Telling et al., 1994). The deg and cyt phenotypes are suppressed when, in addition, the E1A gene is mutated, indicating that these phenotypes are a function of E1A (White et al., 1988). Furthermore, the E1B 21 kD protein slows down the rate by which E1 A switches on the other viral genes. It is not yet known through which mechanism(s) the E1B 21 kD protein quenches these E1A dependent functions.

Vectors derived from human adenoviruses, in which at least the E1 region has been deleted and replaced by a gene-of-interest, have been used extensively for gene therapy experiments in the pre-clinical and clinical phase.

The adenovirus genome is a linear double-stranded DNA molecule of approximately 36,000 base pairs with the 55 kD terminal protein covalently bound to the 5' terminus of each strand. The Ad DNA contains identical Inverted Terminal Repeats (TR) of about 100 base pairs with the exact length depending on the serotype. The viral origins of replication are within the TRs exactly at the genome ends. DNA synthesis occurs in two stages. First, the replication proceeds by strand displacement, generating a daughter duplex molecule and a parental displaced strand. The displaced strand can form a so-called "panhandle" intermediate, which allows replication initiation and generation of a daughter duplex molecule. Alternatively, replication may go from both ends of the genome simultaneously, obliterating the requirement to form the panhandle structure. The replication is summarized in FIG. 1 adapted from (Lechner and Jr., 1977).

As stated before, all adenovirus vectors currently used in gene therapy have a deletion in the E1 region, where novel genetic information can be introduced. The E1 deletion renders the recombinant virus replication (Stratford-Perricaudet and Perricaudet, 1991). We have demonstrated that recombinant adenoviruses are able to efficiently transfer recombinant genes to the rat liver and airway epithelium of rhesus monkeys (Bout et al., 1994a; Bout et al., 1994b). In addition, we (Vincent et al., 1996a; Vincent et al., 1996b; Vincent et al., 1996c) and others (see e.g. (Haddada et al., 1993)) have observed a very efficient in vivo adenovirus mediated gene transfer to a variety of tumor cells in vitro and to solid tumors in animal models (lung tumors, glioma) and human xenografts in immunodeficient mice (lung) in vivo (reviewed (Blaese et al., 1995)).

In contrast to, for instance, retroviruses, adenoviruses a) are able to infect non-dividing cells and b) are able to efficiently transfer recombinant genes in vivo (Brody and Crystal, 1994). Those features make adenoviruses attractive candidates for in vivo gene transfer of, for instance, suicide or cytokine genes into tumor cells.

However, a problem associated with the current recombinant adenovirus vectors is that they do not integrate into the host cell genome. Due to this fact the vector is rapidly lost in dividing tissue. Recently it was demonstrated that integration of adenovirus vectors can be achieved in fertilized oocytes by using extreme multiplicities of infection (Tsukui et al., 1996). In somatic cell gene therapy this is an extremely undesired feature. Efficient integration of adenovirus vectors has also been observed in vitro in cells in which DNA damage was introduced by ionizing irradiation (Zeng et al., 1997). This is a very harsh treatment and not favored in gene therapy protocols.

One of the additional problems associated with the use of recombinant adenovirus vectors is the host-defense reaction against treatment with adenovirus.

Briefly, recombinant adenoviruses are deleted for the E1 region (see above). The adenovirus E1 products trigger the transcription of the other early genes (E2–E4), which consequently activates expression of the late virus genes. Therefore, it was generally thought that E1 deleted vectors would not express any other adenovirus genes. However, recently it has been demonstrate that some cell types are able to express adenovirus genes in the absence of E1 sequences. This indicates that some cell types possess the machinery to drive transcription of adenovirus genes. In particular, it was demonstrated that such cells synthesize E2A and late adenovirus proteins.

In a gene therapy setting, this means that transfer of the therapeutic recombinant gene to somatic cells not only results in expression of the therapeutic protein but also in the synthesis of viral proteins. Cells that express adenoviral proteins are recognized and killed by Cytotoxic T Lymphocytes, which thus a) eradicates the transduced cells and b) causes inflammations (Bout et al., 1994a; Engelhardt et al., 1993; Simon et al., 1993). As this adverse reaction is hampering gene therapy, several solutions to this problem have been suggested, such as a) using immunosuppressive agents after treatment; b) retainment of the adenovirus E3 region in the recombinant vector (see patent application EP 95 20 2213) and c) using ts mutants of human adenovirus, which have a point mutation in the E2A region. However, these strategies to circumvent the immune response have their limitations.

The use of ts mutant recombinant adenovirus diminishes to some extent the immune response, but was less effective in preventing pathological responses in (Engelhardt et al., 1994a).

The E2A protein may induce an immune response by itself and it plays a pivotal role in the switch to the synthesis of late adenovirus proteins. Therefore, it is attractive to make recombinant adenoviruses which are mutated in the E2 region, rendering it temperature sensitive.

A major drawback of this system is the fact that, although the E2 protein is unstable at the non-permissive temperature, the immunogenic protein is being synthesized. In addition, it is to be expected that the unstable protein does activate late gene expression, albeit to a low extent. ts125 mutant recombinant adenoviruses have been tested, and prolonged recombinant gene expression was reported (Engelhardt et al., 1994a; Engelhardt et al., 1994b; Yang et al., 1995; Yang et al., 1994). However, pathology in the lungs of cotton rats was still high (Engelhardt et al., 1994a), indicating that the use of ts mutants results in a partial improvement in recombinant adenovirus technology. An additional difficulty associated with the use of ts125 mutant adenoviruses is that a high frequency of reversion is observed. These revertants are either real revertants or second site mutations (Kruijer et al., 1983; Nicolas et al., 1981). Both types of revertants have an E2A protein that functions at normal temperature and have therefore similar toxicity as. the wild-type virus.

In adeno-associated virus vectors the entire protein coding domain can be replaced by foreign sequences. Adeno-associated virus vectors can integrate into the host cell genome (Kotin, 1994). The only AAV-sequences required in the vector are the inverted terminal repeat elements flanking the foreign DNA. Due to the integrating properties and the absence of viral genes AAV-vectors are very well suited for the permanent genetic modification of target cells in vivo. One drawback is, however, that they are very difficult to produce. Another drawback is the limited packaging size. Only molecules up to approximately 5 kb are efficiently packaged. Another drawback is that rAAV vectors arc delivered as single strand DNA molecules. In the target cell a second complementary strand has to be produced for expression to occur. This does not occur immediately after infection with rAAV. Second strand synthesis is indeed the rate limiting step for expression of the transgene (Ferrari et al., 1996).

SUMMARY OF THE INVENTION

The present invention provides methods and means to combine the integrating capacity of one virus with the large packaging and infection capacity of another virus, as well as the results of these methods and the use of these results. The present invention thus also provides methods to combine the favorable properties of adenovirus vectors with the favorable properties of AAV-vectors.

The present invention provides methods to completely remove all viral genes from the vector thus completely avoiding the cellular immune responses to viral gene products synthesized in the target cell. The only adenovirus sequences necessarily present in the encapsidated DNA are those comprising a functional packaging signal. In cis required sequences for multiplication of vector genomes in the virus producing cell are functional AAV-TR sequences at both ends of the DNA. This Ad/AAV chimeric molecule is replicated in the vector producing cell by the AAV-replication machinery. Packaging of the Ad/AAV chimeric molecules into adenovirus capsids is achieved following expression of the relevant adenovirus genes involved in packaging DNA into adenovirus capsids.

AAV is a non-pathogenic human parvovirus (reviewed in (Berns, 1990a; Berns, 1990b)). The virus replicates as a single strand DNA of approximately 4.6 kb. Both the plus and the minus strand are packaged and infectious. Efficient replication of AAV requires the co-infection of the cell by a helper virus such as Adenovirus or Herpes Simplex Virus. In the absence of a helper virus no substantial replication of AAV is observed. AAV is therefore also classified as a "Dependovirus". When no helper virus is present, the AAV genome can integrate into the host cell genome. The wild-type virus has a strong preference (70%) for an integration site on the long arm of chromosome 19 (19 q13.3) (Kotin et al., 1990; Samulski, 1993; Samulski et al., 1991). This site specificity is probably mediated by the AAV-rep proteins, more specifically by Rep78 and Rep68 (Weitzman et al., 1994). Following integration, the expression of the virus genes is not detectable. The integrated provirus replicates as a normal part of the host cell genome upon division of the transduced cell and ends up in both daughter cells. This stage of the virus life cycle is known as the latent stage. This latent stage is stable but can be interrupted by infection of the transduced cell by a helper virus. Following infection of the helpervirus, AAV is excised from the host cell genome and starts to replicate. During the early phase of this lytic cycle the rep-genes are expressed.

Approximately 12 to 16 hours later the capsid proteins VP1, VP2 and VP3 are produced and the replicated virus DNA is packaged into virions (structure of the AAV-genome and its genes is depicted in FIG. 2). The virions accumulate in the nucleus of the cell and are released when the cell lyses as a result of the accumulation of AAV and the helpervirus (reviewed in (Berns, 1990a; Berns, 1990b)).

The AAV-genome contains two genes rep and cap (FIG. 2). Three promoters (P5, P19 and P40) drive the synthesis of mRNAs coding for 4 Rep-proteins (Rep78, Rep68, Rep52 and Rep40) and three capsid proteins (VP1, VP2 and VP3). The AAV-genome is flanked on both sides by a 145 bp sequence, called the Inverted Terminal Repeat (TR), which appears to contain all the cis-acting sequences required for virus integration, replication and encapsidation (Lusby et al., 1980; Samulski et al., 1989).

The capsid proteins VP1, VP2 and VP3 are produced from a 2.6 kb transcript of the AAV P40 promoter, which is spliced into two 2.3 kb mRNAs by using the same splice donor but two different splice acceptor sites. The splice acceptor sites are located at both sides of the VP1 translation start signal. VP1 is translated from the messenger that uses the splice acceptor directly in front of the VP1 translation initiation codon. VP2 and VP3 are translated from messengers that are spliced to the acceptor 3' of the VP1 ATG. VP2 and VP3 are translated from this messenger by use of an ACG translation start (VP2) or a downstream ATG (VP3). Since all three coding regions are in frame, the capsid proteins share a large domain with an identical amino-acid sequence. VP3 is entirely contained within VP1 and VP2, but the latter two contain additional amino-terminal sequences. Similarly, VP1 contains the entire VP2 protein but carries an additional N-terminal sequence. All three capsid proteins terminate at the same position (Ruffing et al., 1994). The AAV capsid is 20 to 24 nm in diameter (Berns and Bohensky, 1987; Srivastava et al., 1983) and contains approximately 5% VP1, 5% VP2 and 90% VP3. This ratio is believed to reflect the relative abundance of the alternatively spliced messengers and the reduced translation initiation efficiency at the ACG initiation codon for VP2.

During a productive infection, the P5-promoter is activated first and directs the production of the large Rep-proteins, Rep78 and Rep68. These proteins are essential for AAV-replication and in trans regulate the expression of viral and cellular genes. The large Rep-proteins activate the P19 and the P40 promoter. In a latent infection, however, Rep78 and Rep68 down regulate expression of the P5 promoter and help to maintain the latency of AAV (for a review see (Berns, 1990b)). The smaller Rep-proteins, Rep52 and Rep40 are encoded by transcripts from the P19 promoter and are important for the formation of infectious virus (Chejanovsky and Carter, 1989). The P40 promoter is the last promoter to become activated and its activation follows the expression of the late genes of the helper adenovirus. Via alternative splicing different mRNA are produced coding for the structural proteins VP1, VP2 and VP3 (Trempe and Carter, 1988).

DETAILED DESCRIPTION OF THE INVENTION

Figure 1:
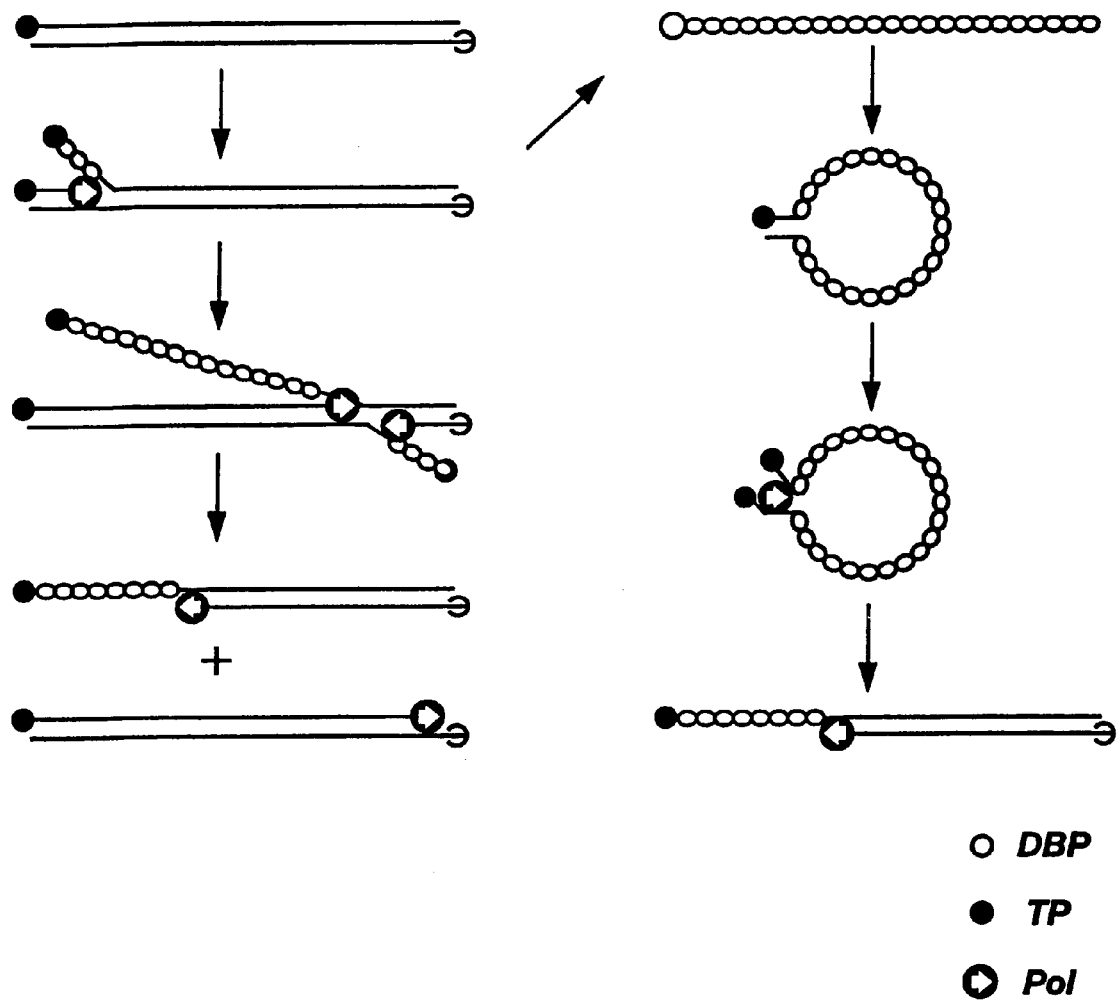
FIG. 1: Schematic representation of adenovirus replication. Indicated are DNA binding protein (DBP), Terminal protein (TP) and Polymerase (Pol).
Figure 2:
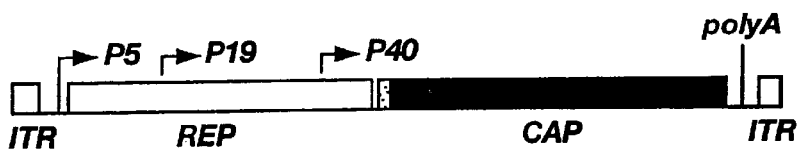
FIG. 2: depicts the structure and the genome organization of wtAAV. The AAV rep and cap genes are flanked by two inverted terminal repeats (ITR). Indicated are the three identified promoters (P5, P19 and P40) and the common polyadenylation signal. Five different species of mRNA have been-identified from which Rep78, Rep68, Rep52, Rep40, VP1, VP2 and VP3 are translated. VP2 and VP3 are translated from the same message. VP2 translation starts at an ACG codon indicated with an asterisk.
Figure 2:
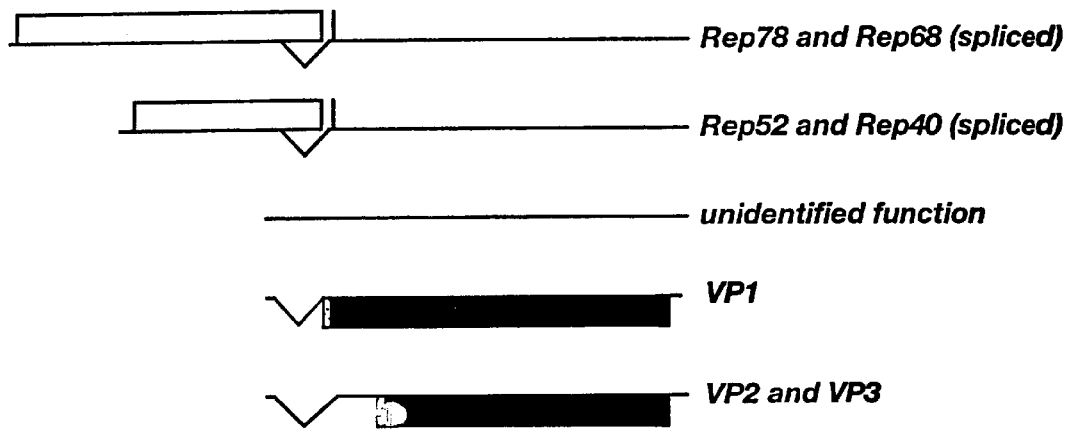

In the present invention components of non-integrating and integrating viruses are combined to yield a new class of recombinant viruses with properties derived from both original viruses.

Preferably, the integration process is dependent on host cell factors only. In this case, only the cis-acting sequences required for the integration process are supplied to the target cell. When the integration process is also dependent on transacting factors that are not normally present in the target cell, the transacting factors can be supplied by the recombinant virus. This can be achieved either through co-packaging of the factors into the virus particle or through the incorporation of the transacting factors encoding genes in the recombinant virus followed by expression of the transacting factors encoding genes in the target cell. Thus, the invention provides a chimeric viral vector comprising a functional packaging signal derived from a first virus having a large insertion capacity and an integration means derived from an integrating second virus. A functional packaging signal is intended to read on any signal derived from a virus which leads to packaging with packaging material of said virus. This may be a part of the original signal or a modified signal produced in any possible way. The same goes for the integration means. This may be the original means, but also a fragment or a derivative thereof. In this way the best of both worlds is achieved. The large insertion which usually cannot be packaged into integrating vectors can now be stably integrated into the genome of the target cell. Preferably the virus which is going to provide the outside of the new chimeric virus is a virus which is capable of efficiently infecting the target cell. Typically such a virus is an adenovirus.

The preferred integrating virus is an adeno-associated virus. If the chimeric vector comprises AAV Tr's, then it is preferred to include the rep gene of AAV to provide for site-specific integration at a known safe site.

Of course, the vector needs to include a sequence of interest. A sequence of interest can be one or more genes or an antisense sequence, etc.

The diseases or conditions to be treated with gene therapy and the sequences of interest suitable therefore are well known in the art and need no further explanation here. The sequences of interest usually need to be expressed and therefore regulatory elements such as (inducible) promoters for said expression are preferably present on said vectors. In order to be able to, switch off whatever cell that has been genetically modified with a vector according to the invention it is preferred to provide said vector with an additional suicide gene, which can be induced to eliminate the modified cell (such as TK).

In order to be able to infect cells, the vectors should be packed into virus-like particles. Such a virus-like particle comprises a vector as disclosed above and capsid elements. Preferred are adenovirus-like particles. Herein, methods to produce these particles (or viruses) are given. Usually, a packaging cell will be employed. Packaging cells are typically cells which have been provided with all remaining genes for the virus to be produced. In these cells, a vector as disclosed above is brought to be (replicated) and packed. Sometimes all elements for packing are provided by the cell, and sometimes a number are present on the vector to be packed (or packaged). The cells can be provided with these elements by using yet another viral vector which either integrates or stays episomal, but which preferably cannot be packed into the same materials as the vectors according to the invention. The invention is illustrated with a chimeric adenovirus/adeno-associated virus vector, but the invention is not limited to these viruses. The chimeric adenovirus/adeno-associated virus vectors described in the present invention minimally contain the sequence of interest linked (directly or indirectly) to a functional adenovirus packaging signal. The linked sequences are flanked by functional AAV-TR. Replication of the molecule is directed by the AAV-replication machinery, while the molecule is packaged by the structural proteins of adenovirus. The two processes, replication and packaging, can occur simultaneously and interact with each other. AAV-TR containing adenovirus vectors have been described before (Thrasher et al., 1995). In these cases, a rAAV-vector was incorporated into an adenovirus vector. Both in the virus producing cell and in the target cell, these molecules behave as classical E1-deleted adenovirus vectors. No integration of the whole or parts of the adenovirus vector was detected. In our opinion, this is due to the fact that the AAV-TR in these recombinant adenovirus vectors are physically linked on both sides to DNA of the vector. To mediate integration of the AAV-TR in these molecules, the rAAV present in the adenovirus vector must first be rescued from the vector before the TR can catalyze the integration of the rAAV vector. This rescue process is not efficient in the absence of a productive AAV-replication. In addition, these rAAV containing recombinant adenovirus vectors contain many adenovirus genes and are not suited for the incorporation of large DNA fragments.

Description of the Recombinant Molecules of the Invention

In its simplest form, the invention provides a molecule comprising a gene of interest directly or indirectly linked to a functional (adenovirus) packaging signal flanked by integrating capability such as AAV-TR. This simple molecule is designated minimal Ad/AAV chimera. The entire group of Ad and AAV chimeric molecules are termed Ad/AAV chimera or chimeric vectors. Important components of the present invention are the chimeric Ad/AAV-vector and methods, vectors and cell lines to produce the chimeric vector.

In one embodiment of the invention the chimeric vector comprises a sequence of interest, an adenovirus packaging signal and two AAV-TR. In cis can be added an adenovirus TR sequence for improved packaging. Production and packaging of the chimeric vector is achieved in cells that supply the in trans required proteins for replication and packaging of the chimeric virus. In this preferred embodiment the chimeric vector is completely devoid of viral protein coding domains. In another preferred embodiment certain viral genes are present in the viral vector. These genes can be expressed in the chimeric virus producing cell and/or in the target cell to perform specific tasks. One example is a chimeric Ad/AAV molecule in which all Adenovirus genes except E1 are present between the AAV-TR together with a gene of interest and an adenovirus packaging signal. This recombinant virus can be generated in cells that express the adenovirus E1-gene such as PER.C6 and the AAV-rep gene (for instance through transfection of a rep-expression plasmid).

It is obvious to persons skilled in the art that between no adenovirus genes and all adenovirus genes there are many different combinations possible. Specific combinations can be tailored by adding some viral genes to the minimal components of the chimeric vector and supplying the remaining viral gene products in trans. Specific advantages of special configurations are clear to the person skilled in the art. For instance, a current active field of interest is to remove all the adenovirus early genes from classical adenovirus vectors to circumvent cellular immune response to adenovirus vector infected target cells. In the minimal vector these can be deleted while retaining the adenovirus late gene functions. The adenovirus early genes necessary for efficient AAV-replication (E1, E2, E4 and VA) can be supplied in trans.

In an especially preferred embodiment, the AAV-rep-gene is added to chimeric Ad/AAV molecules described above. Preferably, the AAV-rep gene is under transcriptional control of the AAV-p5-promoter. In the virus producing cell, rep-gene expression from the chimeric construct will obviate the need to produce the rep-gene products through different means. In the target cell, rep-expression will facilitate targeted integration of the chimeric vector into chromosome 19 in the region 19q13.3-qter (Balague, 1997; Surosky et al., 1997).

The preferred location of the functional Adenovirus packaging signal in the chimeric molecule is near one of the AAV-TR. Moving the Adenovirus packaging signal more toward the middle of the molecule is expected to lower the efficiency with which the molecule is packaged into Adenovirus capsids.

In a preferred embodiment of the invention, the total size of the chimeric virus, based on Ad/AAV chimera, is more than 27.000 bases, the lower limit of efficient packaging in adenovirus capsids, but not more than approximately 40.000 bases, the upper limit of packaging into adenovirus capsids. In a preferred embodiment, the appropriate size of the chimeric virus is achieved by inserting the appropriate amount of DNA-sequences via standard molecular cloning techniques. In another preferred embodiment the appropriate size is generated in the virus producing cell. In chimeric viruses based on Adenovirus and AAV, this can be achieved by relying on the packaging of replication byproducts and/or replication intermediates. For AAV-mediated replication a packageable replication byproduct would be the duplex dimer of 30 kb, when the monomer is approximately 15 kb. When the duplex dimer is packaged, each adenovirus capsid contains the DNA of two instead of one chimeric viruses. Higher order concatemers can also be packaged provided that the size of the monomer is adjusted appropriately.

In a preferred embodiment of the invention, the TR flanking the sequence of interest and the adenovirus packaging signal in the chimeric molecule are derived from AAV, while the replication of the molecule is promoted by AAV-rep. However, TR-sequences of autonomous parvoviruses, such as B19 and MVM, are also suitable for this purpose. These TR-sequences will also promote integration of the chimeric virus in target cells. Moreover, the replication of these autonomous parvoviruses is independent of a helpervirus, thus simplifying the production process.

Production of the Ad/AAV Chimeric Molecules

In a preferred embodiment, trans complementation of viral genes is achieved by transfection of the trans requirements into the cells. The trans required adenovirus genes can be cloned into a plasmid or a cosmid. The adenovirus TR-sequences can be retained during the cloning process but the adenovirus packaging signal must be removed to avoid packaging. Preferably the genome organization of adenovirus is maintained. If clones are used that contain the trans-acting genes of adenovirus flanked by adenovirus TR, then adenovirus-mediated replication of the transacting genes in the chimeric virus producing cell can lead to a higher expression of the in trans required adenovirus functions. This enables enhanced production and packaging of the chimeric virus. These molecules can be obtained by persons skilled in the art. In another preferred embodiment, stable packaging cell lines are used to complement certain or all in trans requirements. Trans complementing cell lines can be generated by stability transfecting the relevant viral genes into human cells using constitutive expression systems or inducible expression systems. Stable cell lines expressing AAV-rep have been reported (Clark et al., 1995; Clark et al., 1996; Holscher et al., 1994) and WO 97/20943 and are suited to complement this trans requirement. Stable cell lines expressing adenovirus E1, E2 and/or E4 and VA have also been reported and can also be used to complement these requirements of the chimeric vector. Stable cell lines capable of expressing the adenovirus late genes can be generated by using a conditional chromosomal excision and replication system as described in European patent application 972003245. It is clear to persons skilled in the art that transient transfection can be combined with stable packaging cell lines to generate the chimeric viruses. One example is to combine stable cell lines that are able to express the adenovirus E1 and E4 proteins with a transient transfection with a plasmid or plasmids containing adenovirus E2, VA and the adenovirus late function and an expression cassette for the AAV-rep gene. Particularly preferred are packaging cell lines expressing adenovirus E1 and that conditionally express the AAV-rep proteins. These can be generated using cells suitable for the constitutive expression of E1 (Fallaux et al., 1996; Graham et al., 1977) and using regulatable promoters for the expression of AAV-rep. A special property of the regulatable promoter is that it is not activated by adenovirus E1 genes.

In a particularly preferred embodiment, trans complementation for the production of chimeric viruses is achieved by virus infection, a process which can easily be scaled up to produce the chimeric vector in large amounts. In its simplest form, this can be achieved by infecting cells with wtAAV and wtAd. However, this is not practical since, in this case, wtAAV and wtAd are also produced together with the chimeric virus. This is not desired in a gene therapy product. A more sophisticated approach is to incorporate the trans complementing adenovirus and/or AAV genes in, for instance, Herpes Simplex Virus (Johnston et al., 1997) or vaccinia virus. Another method is to generate a recombinant adenovirus containing a functional adenovirus packaging signal and all adenovirus genes except E1 and E2B (AdDE1, E2B). This AdDE1, E2B recombinant virus can be grown on cells expressing E1 and E2B (Amalfitano and Chamberlain, 1997). Production of chimeric viruses can be achieved in cells expressing E1 and AAV-rep. The AdDE1, E2B recombinant viruses are replicated in E1, E2B expressing cells but not in chimeric virus producing cells due to the absence of E2B in the chimeric virus producing cell. E2B contains the genes for preterminal protein and the polymerase. The proteins are essential for adenovirus replication but not for AAV replication (Muzyczka, 1992).

In cases where an adenovirus or a recombinant adenovirus is used to complement in part or in whole the in trans requirements, another preferred embodiment of the invention provides a protein required for adenovirus but not for AAV mediated replication which is conditionally expressed. Conditional expression can be achieved, for instance, by using a conditional expression system or by using a temperature sensitive mutant. Conditional expression of a protein crucial to adenovirus replication but not to AAV-replication enables the regulation of the replication and packaging process. Disabling adenovirus replication in the early stages of the production process aids a higher accumulation of replicated chimeric virus. By inducing the expression of the protein required for adenovirus replication later in the production process, adenovirus late functions are upregulated late in the production process.

Production of the chimeric virus can be achieved also by means of methods for the production of minimal adenovirus vectors, such as the recently described so-called cre-lox system (Parks et al., 1996; Parks and Graham, 1997), by additionally supplying the required AAV-rep proteins in trans.

The invention in one embodiment provides methods to surpass the packaging limitation of AAV-vector. The invention further circumvents the necessity for second strand synthesis in the target cell. Second strand synthesis is the rate limiting step in AAV-vector transduction (Ferrari et al., 1996). The invention further provides methods for the production of minimal adenovirus vectors devoid of viral genes. The invention also provides methods for the integration of adenovirus vectors. The invention in yet another embodiment provides methods for the long term persistence of vector transduced cells. The invention provides methods for the stable genetic modification of human cells. The invention is also useful for the- stable genetic modification of plant cells or insects. In these instances, the gene of interest flanked by AAV-TR sequences is packaged into plant or insect cell specific DNA virus capsids. The invention is useful for the generation of transgenic animals through infection of germ-line cells or ES cells with the chimeric viruses. The invention provides methods for the long term persistent expression of foreign genes in vivo. The invention provides methods to facilitate homologous recombination particularly useful for gene replacement strategies.

Viruses according to the present invention can be applied in any and all gene therapy concepts conceived so far. Typically, the person skilled in the art will be able to assess for which applications the viruses of the present invention are especially suitable. Thus the invention will find application in the treatment of inherited diseases and diseases resulting from functional deletion of certain gene functions (such as cystic fibrosis and the like). It will also find application in combating malignancies by delivering suicide or other cell death inducing agents to aberrant cells. In this manner, it will also find application in (auto) immune diseases. It is not necessary that the virus always delivers a gene to the target cell. It may very well be that the virus delivers a sequence being or encoding an antisense sequence to suppress the expression of a gene of the host cell. The sequence may also be or encode a cosuppressing sequence. The virus may also deliver more than one sequence of interest to a target cell. For instance, a'suicide gene may be added next to a gene (or other sequence) of interest to enable elimination of the transduced cells if they become aberrant or are no longer wanted.

The chimeric viruses of the invention are particularly useful for the stable modification of target cells and the introduction of relatively large DNA-fragments (between approximately 27 kb and 40 kb). In a preferred embodiment of the invention, the property of transferring large DNA fragments is used to transfer the cDNA of large genes, such as Factor VIII, Von Willebrandt Factor and Dystrophin or mucins involved in the formation of the mucus lining in, for instance, the gastro-intestinal tract. In another preferred embodiment, the molecules of the present invention are used to transfer genes together with large genomic DNA regions required for accurate expression of the gene of interest. Examples of large DNA regions with effect on the expression of foreign genes are intron-sequences, locus control regions (LCR) and boundary regions. Some genes, like the human β-globin gene, require intronic sequences to be present for efficient expression. Locus control regions, such as the β-globin locus control region, are usually found on large DNA-fragments. Boundary elements may be present in small molecules which retain activity. However, the activity is usually less than observed in the authentic genomic environment. Segmentation of the large fragment combined with fine mapping of the active elements can help to delete redundant DNA-sequences and help to generate smaller molecules with similar activity as the original fragment in the natural configuration. This process can result into DNA fragments with sizes that can be incorporated into, for instance, AAV or retroviruses which have of packaging limit below 10 kb. However, activity of these in sized reduced artificial introns or locus control regions can not be predicted beforehand and indeed these in sized reduced regions rarely behave the same as the unmanipulated regions (Einerhand et al., 1995; Ellis et al., 1997; Ellis et al., 1996; Fiering et al., 1995; Li and Stamatoyannopoulos, 1994). The molecules of the present invention enable designers of expression cassettes to incorporate significantly larger regions of DNA and, thus, facilitate the generation of cassettes with predictable expression characteristics.

As used herein, the term "gene" refers to a nucleic acid molecule encoding a protein and/or RNA.

As used herein, the term "wtAAV" refers to a nucleic acid molecule containing the genes rep and cap derived from AAV serotypes 1, 2, 3, 4 or 5 or functional analogs or parts thereof physically linked to two AAV-ITR.

As used herein, the term adenovirus refers to a adenovirus type 5 or functional analogs or parts thereof. However, for the present invention adenovirus type 1 to 4 and 6 to 51 are also suitable.

As used herein, the term "recombinant AAV vector" means a nucleic acid molecule comprising at each end an AAV-ITR.

As used herein, the term "replication" with respect to viral DNA refers to a process of multiplication of a nucleic acid molecule distinct from the normal replication of eukaryotic chromosomal DNA in that not just one but, indeed, many copies of the replicating molecules are formed in a cell during the process.

As used herein, the term "replicating DNA molecule" refers to a DNA molecule which can undergo replication in a cell. The replication can start from an integrated DNA molecule or from a DNA molecule that is present in the nucleus of a cell as an episome.

It will be understood that the term "packaging cell" means a cell line that provides in trans the required AAV-proteins and adenovirus proteins necessary for the replication and/or packaging of chimeric viruses. The in trans required proteins are provided either in a constitutive fashion or in a regulated fashion or a combination of both. The in trans required proteins are provided though expression from their encoding genes either from integrated or from episomal gene copies or a combination of both. Episomal DNA can be introduced by means of transfection (a process termed "transient transfection") or infection.

It will be understood that the term "trans requirements" means genetic information which is required to be present in the same cell as the chimeric virus but which is not required to be physically linked to the chimeric virus. Trans requirements are usually expressed genes from which either the RNA or the protein is functional.

It will be understood that the term "trans complementation" means the act of supplying the trans requirements for the chimeric virus.

As used herein, the term "XL-rAAV" refers to a nucleic acid molecule of more than 6.5 kb up to at least 33 kb physically linked to and flanked by two AAV-ITR. The AAV-medication replication of large DNA molecules is useful not only for the replication and production of Ad/AAV chimeric molecules but may also find its use in other applications.

XL-rAAV replication in a cell, can be observed upon expression in a permissive cell of functional amounts of the proteins encoded AAV-rep and functional amounts of the proteins encoded by adenovirus 5 regions E1, E2a, E4, or functional parts or derivatives of said proteins and, optionally, RNA encoded by an adenovirus 5 VA-region. One or more of said protein may be omitted. For instance but not limited to, Rep52 and/or Rep40. Rep78 and Rep68 possess similar functions. Thus, a decrease in the amount of one protein may, at least in part, be compensated by an increase in the amount of the other protein.

An XL-rAAV may comprise an adenovirus packaging signal and or an adenovirus TR but this is not essential for replication of the molecule. Higher amounts of replicated XL-rAAV may be obtained, particularly in the presence of a replicating adenovirus (vector), by increasing the level of E2a protein in the cell over the level of E2a produced by the E2a-gene in its native configuration. Such additional E2a may be supplied in many different ways, such as, but not limited to, co-transfection of an E2a-expression plasmid or modifying the promoter sequences driving the E2a-gene expression in an adenovirus vector.

One or more of the proteins directing XL-rAAV replication may be provided by other proteins provided that they provide similar functions. For instance, Rep-proteins may be derived from AAV-2 but may also be derived from Rep-proteins or functional parts or derivatives thereof from other serotypes. Currently, six different primate AAV serotypes are identified. However, also AAV from other animal species may be used for the same purpose. By analogy, adenovirus proteins may be derived from adenovirus 5 but may be substituted by adenovirus proteins, or functional parts or derivatives thereof, from other serotypes exhibiting similar functions. Similarly, AAV-ITR may be derived from AAV-2 but also from other AAV serotypes or AAV isolated from animals other than primates.

AAV or adenovirus proteins promoting XL-rAAV replication in a cell may be substituted by proteins or a mechanism providing similar function. Such protein or mechanism may be of natural origin or artificial.

Requirements for the replication of the XL-rAAV may be provided on a DNA molecule that is physically separated from a DNA molecule comprising an XL-rAAV or one or more requirements may be covalently attached to a molecule comprising an XL-rAAV.

A cell comprising a XL-rAAV may be used for the production of proteins, Ad/AAV chimeric molecules of the present invention, minimal adenovirus vectors, recombinant AAV vectors, lentivirus vectors, retrovirus vectors, herpes simplex virus vectors and other virus vectors.

In one embodiment, the invention provides a rAAV nucleic acid, termed XL-rAAV, with a genome size at least larger than 6.5 kb. In another embodiment the invention provides rAAV nucleic acid, termed XL-rAAV, with a genome size at least larger than 13 kb.

In one embodiment, the invention provides a method for the replication of XL-rAAV comprising providing a cell, preferably a primate cell, with proteins encoded by an AAV-rep gene or parts or derivates thereof, proteins encoded by adenovirus regions E1, E2 and/or E4 or parts or derivatives thereof of said proteins, optionally with RNA encoded by adenovirus VA-regions or parts or derivatives thereof and further providing said cell with a nucleic acid comprising a XL-rAAV. In a preferred aspect of the invention, said cell is a cell in which the replication of other viral nucleic acid than XL-rAAV nucleic acid, preferably adenovirus nucleic acid, is at least in part repressed. In a preferred aspect of the-invention said replication of XL-AAV is used for the packaging of XL-AAV into a virus-like particle according to the invention. In a preferred embodiment of the invention said replication of XL-AAV is used for the packaging of XL-AAV into an adenovirus-like particle, in which case, said XL-AAV preferably includes an adenovirus packaging signal and/or an adenovirus TR.

In one embodiment of the invention, a self-replicating molecule is provided. Said self-replicating molecule comprises physically linked and, preferably but not necessarily, within AAV-ITR, sequences encoding proteins from adenovirus regions E1, E2a and/or E4 (or parts or derivatives or functionally equivalent counterparts thereof) together with the AAV-rep-gene (or parts or derivatives or functionally equivalent counterparts thereof) and a sequence of interest. Said self-replicating molecule may be used for the expression of proteins encoded by said sequence of interest. In a preferred aspect of the invention said sequence of interest comprises means for the production of lentivirus vectors. In another preferred embodiment said sequence of interest comprises means for the production of adenovirus vectors.

Materials and Methods

General Methods

Restriction enzymes were purchased from GIBCO BRL, Life Technologies (Breda, The Netherlands) except for Nsi I and Ahd I which were purchased from Biolabs (Leusden, The Netherlands). Restriction enzyme digestions were carried out according to manufacturer's protocols. HeLa cells and PER.C6 cells were maintained in Dulbecco's modified Eagles Medium (DMEM, GIBCO BRL, Life Technologies, Breda, The Netherlands) supplemented with 10% heat-inactivated Fetal Bovine Serum (FBS, GIBCO BRL, Life Technologies, Breda, The Netherlands) and 50 µg/ml gentamnicin (GIBCO BRL, Life Technologies, Breda, The Netherlands).

Generation of Minimal Ad/AAV Chimeric Constructs

Description of the Constructs:

We generated three different Ad/AAV chimeric constructs. All constructs have the adenovirus packaging signals in between AAV-TR. They also all contain a nuclear targeted β-galactosidase (*Escherichia coli*) reporter gene under the control of the immediate-early enhancer/promoter sequences of the cytomegalovirus (CMV). The constructs differ in the adenovirus sequences used to enhance packaging of the DNA into Ad particles. In one construct pTR-AdyLacZ, we included Ad5 nuclectides 104 until 454 in the construct. This sequence encompasses the viral packaging signal between nucleotides 194 and 380, identified by (Graeble and Hearing, 1990; Graeble and Hearing, 1992; Hearing et al., 1987; Schmid and Hearing, 1997). Currently it is not known whether Ad TR sequences have a role in packaging (Graeble and Hearing, 1990; Graeble and Hearing, 1992; Hearing et al., 1987; Schmid and Hearing, 1997). For this reason we generated the construct TR-AdTRyLacZ, with the Ad5 sequences 1 until 454, containing both the Ad packaging signal and the Ad TR. The third construct, pTR-D18AdTRyLacZ also contains the Ad packaging signal and the Ad TR but in this case the first 18 nucleotides, which contain the pTP-Pol binding site, were deleted to avoid possible interference of the Ad-replication machinery with the AAV-replication machinery.

Generation of the Constructs:

The Ad packaging signal was amplified from plasmid pCMV.nls.lacZ (Fortunati et al., 1996) which contains the native Ad5 sequences 1–454. The three PCRs were performed with a standard 3' primer and different 5' primers. The 3' primer was 5'-<u>GGAAGCTTAGATCTGCGGCCGC</u>-CTGACTATAATAATAAAACG-3' (SEQ. ID. NO.: 1). For cloning purposes a HindIII, a BglII and a NotI restriction site were introduced at the 3'-end of the fragment (underlined). The 5' primer for Ad y was 5'-CCAAGCTTAGATCTTA-GTGTGGCGGAAGTGTGATG-3' (SEQ. ID. NO.: 2). The 5' primer for Ad TR y was 5'-CCAAGCTTAGATCTCATCATCAATAATATACCTTA-3' (SEQ. ID. NO.: 3) and the 5' primer for D18 AdTR y was, 5'-CCAAGCTTAGATCTTTATTTTGGATTGAAGCCAA-TATG-3' (SEQ. ID. NO.: 4). For cloning purposes the restriction sites HindIII and BglII were introduced into the 5'-end of the fragment. The PCR reactions were performed with 5 ng template (pCMV.nls.lacZ) and Pwo DNA polymerase (Boehringer Mannheim, Almere, The Netherlands) using the buffer and the reaction conditions recommended by the manufacturer. Samples were heated for 2 min. at 94° C. followed by 30 cycles of 94° C. 30 seconds, 55° C. 45 seconds and 68° C. for 2 minutes. After cycling the reaction mixture was incubated for an additional 10 minutes at 68° C. The PCR-fragments were run on 1.5% agarose gels and purified using the Recovery DNA purification Kit II (Hybaid, Teddington, Middlesex, UK) according to the manufacturer's protocol. The products were digested by HindIII and cloned into HindIII-digested pUC119 (GIBCO BRL, Life Technologies, Breda, The Netherlands) to generate respectively pAdy, pAdTRy and pD18AdTRy. The amplified elements were sequenced (BaseClear, Leiden, The Netherlands) and found to be without mutations. Next we introduced into the clones the β-galactosidase (*Escherichia coli*) reporter gene under the control of the CMV immediate early enhancer/promoter and the SV40 polyadenylation signal (CMV LacZ). The CMV LacZ insert was amplified by Expand Long Template PCR (Boehringer Mannheim, Almere, The Netherlands) from plasmid pCMV.nls.LacZ plasmid according to the manufacturer's protocol. The upstream primer had the sequence; 5'-GCGTGGCCA GCGGCCGCATCGATACTAGTCAGGTCGTTACATAA-CTTACGG-3' (SEQ. ID. NO.: 5), whereas the. downstream primer had the sequence; 5'-CGCCTT GCGGCCGCCACGTGCGGTACCCCGCCACACTCGC-AGGGTCTGCA-3' (SEQ. ID. NO.: 6). For cloning purposes NotI, ClaI and SpeI restriction sites (underlined) were introduced in the upstream primer. In the downstream primer NotI, PmlI and KpnI restriction sites were introduced (underlined). The PCR-reactions were performed using 5 ng template plasmid. The mixture was heated at 94° C. for 2 minutes followed by 30 cycles of 94° C. for 30 seconds, 55° C. for 45 seconds and 68° C. for 4 minutes. PCR-reactions were followed by an incubation at 68° C. for 10 minutes. Fragments were run on 0.8% agarose gels and purified using the Recovery DNA purification Kit II as described previously. The PCR product was NotI digested and ligated into NotI-digested pAdy, pAdTRy and pD18AdTRy to yield the plasmids. pAdyLacZ, pAdTRyLacZ and pD18AdTRyLacZ, respectively. To demonstrate β-galactosidase function the plasmids were transfected into PER.C6 cells (described below).

Figure 3:
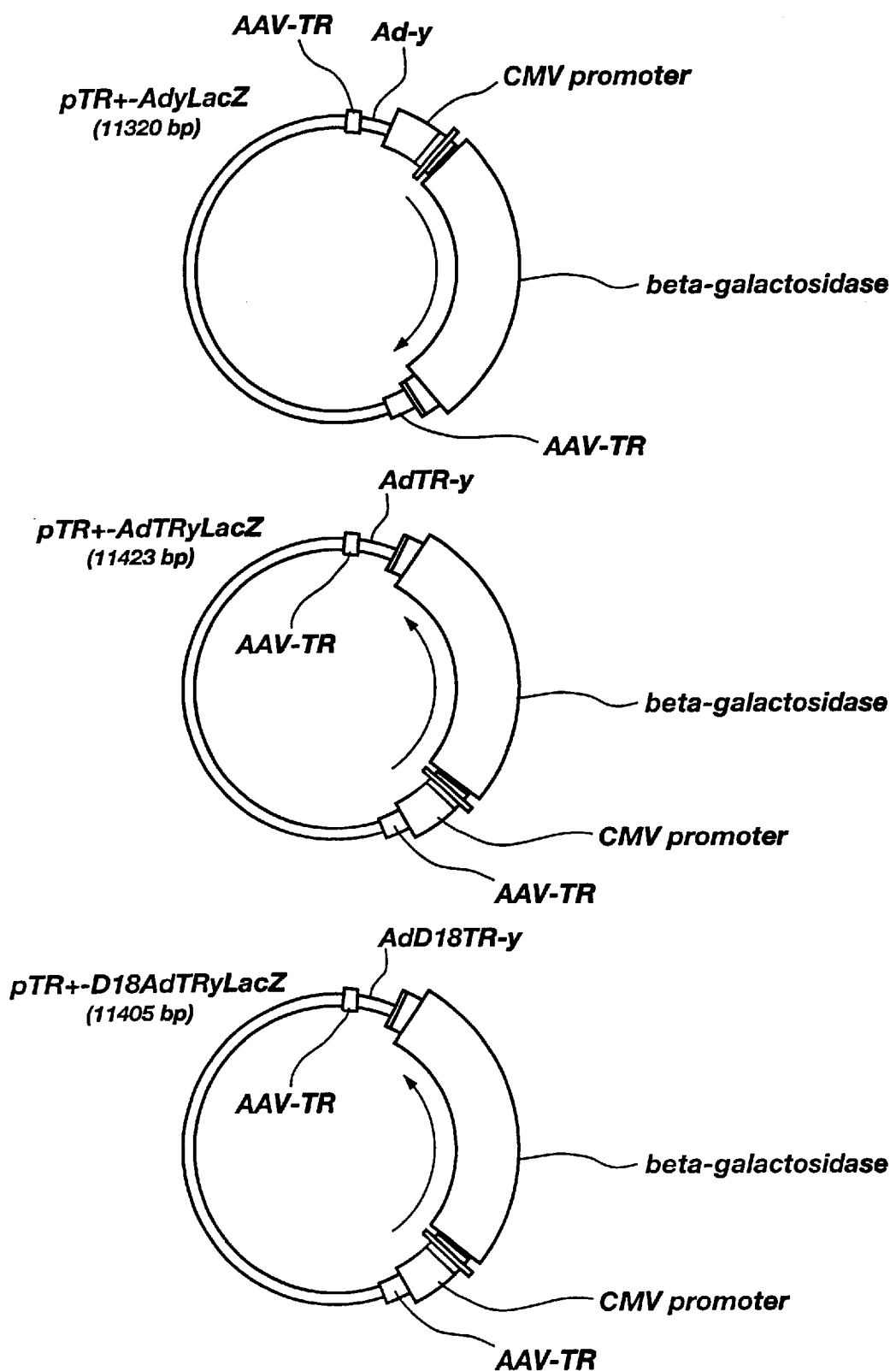
FIG. 3: Schematic representation of the plasmids containing the minimal Ad/AAV chimeric virus. The three constructs have the adenovirus packaging signals in between AAV-TR. They also all contain a nuclear targeted beta-galactosidase (*Escherichia coli*) reporter gene under the control of the immediate-early enhancer/promoter sequences of the cytomegalovirus (CMV). The orientation of the CMV beta-galactosidase expression cassette in the construct is indicated by an arrow. The constructs differ in the adenovirus sequences used to enhance packaging of the DNA into Ad particles. In construct pTR⁺-AdyLacZ, Ad5 nucleotides 104 until 454 were included in the construct (Ad-y). In construct pTR⁺-AdTRyLacZ, Ad5 sequences 1 until 454, containing both the Ad packaging signal and the Ad TR, were included (AdTR-y). In construct pTR⁺-D18AdTRyLacZ, Ad5 sequences 19 until 454 were included (AdD18TR-y).

The minimal Ad/AAV chimeric constructs pTR-AdyLacZ, pTR-AdTRyLacZ and pTR-D18AdTRyLacZ were generated as follows. The plasmids pAdyLacZ, pAdTRyLacZ and pD18AdTRyLacZ were digested with BglII. The fragments containing the Ad-packaging signal, the CMV-LacZ and, for pAdTRyLacZ and pD18AdTRyLacZ, the relevant parts of the AdTR were isolated and ligated into the .BglII-site of pAAV-TR. The final constructs are depicted in FIG. 3. pAAV-TR was derived from plasmid pTR (a kind gift from Dr. S. Zolotukhin) by transferring the PstI-fragment containing a 1270 bp BglII fragment from Ad5 flanked by AAV-TR into the NsiI-site of the cosmid vector pWE25. The cosmid pWE25 was derived from pWE15 (Clontech, Heidelberg, Germany) in two cloning steps. First pWE20 was generated through ligation of the 4000 bp and 2357 bp fragments of a PstI-digest of pWE15. Correct ligation of the fragments resulted in restoration of the bacterial ampicilin resistance gene. Subsequently the cosmid pWE20 was digested with HindIII and ClaI and blunted with large fragment DNA polymerase (Klenow, GIBCO BRL, Life Technologies, Breda, The Netherlands). The blunted molecule was ligated to a 5' phosphorylated double stranded oligonucleotide with the palindromic sequence, 5'-CGATGCATCG-3' (SEQ. ID. NO.: 7) encoding an NsiI-site to give the final cismid pWE25. The insertion of the oligonucleotide has been confirmed by Nsi I digestion and by DNA sequencing.

Molecular clones of each of the three minimal Ad/AAV chimeric constructs were screened by restriction enzyme digestion pattern analysis. Clones that showed the expected migration pattern were subjected to further analysis by using the restriction endonucleases AhdI and BglI. On each AAV TR there is one restriction site for these two enzymes. Thus the absence of one or more of these sites indicates rearrangement of the AAV-TR in that particular case.

Biological Functionality of PCR Amplified CMV-LacZ

The PCR amplified LacZ reporter gene and associated control elements (CMV LacZ) were evaluated for biological activity in PER.C6 cells by calcium phosphate precipitation (GIBCO BRL, Life Technologies, Breda, The Netherlands). The constructs pAdyLacZ, pD18AdTRyLacZ and pAdTRy-LacZ were transfected into, approximately, 70% confluent PER.C6. Approximately 24 hours after transfection, fresh medium was added to the cells. After another 24 hour period, the transfected cells were stained for LacZ activity.

*E. coli* βGalactosidase Activity Staining

Cells were washed twice with PBS (NPBI, Emmer-Compascuum) and subjected to fixation for 10 minutes by 0, 2% glutaraldehyde solution (Sigma, Zwijndrecht, The Netherlands) in PBS. The cells were washed twice with PBS and stained with X-Gal solution (2 mM $MgCl_2.6H_2O$, 5 mM $K_2Fe(CN)_6$, 5 mM $K_4Fe(CN)_6.3 H_2O$ and 40 mg/ml X-Gal (5-bromo-4chloro-3indolyl-β-galactopyranoside, Molecular Probes Europe, Leiden, The Netherlands) in 0,1 M phosphate buffer). After overnight staining at 37° C. blue cells were counted under an optical microscope (Olympus CK2-TR).

Rescue and Replication of Minimal Ad/AAV Chimeric Constructs

PER.C6 were transfected using Lipofectamine (GIBCO BRL, Life Technologies, Breda, The Netherlands) with minor modifications to the protocol of the manufacturer. For each transfection 60% confluent 25 cm2 flasks received a total of 8 µg of DNA and 40 µl Lipofectamine. AAV-rep proteins were supplied by transfection of pDRBE-rep. The plasmid pDRBE-rep contains the AAV nucleotides 244 till 2596 spanning the entire rep-protein coding domain. In the p5-promoter nucleotide 266 till 277 have been substituted for a SphI and SpeI restriction enzyme site. The ratio of Ad/AAV construct to rep-containing construct was 1 to 4 (mg/mg). In cases where only the minimal Ad/AAV chimerical constructs were transfected, the total amount of 8 µg of DNA was reached by adding the appropriate amount of hearing sperm DNA (GIBCO BRL, Life Technologies, Breda, The Netherlands) into the transfection mixtures. The liposome/DNA complexes were allowed to form for 30 minutes. Meanwhile, the cells were washed with 5 ml of DMEM. DMEM (2, 3 ml) was added to the transfection mixture and the mixture was added to the washed cells. At this point the helper adenovirus IG Ad CMV Luc (EP 95202213) was added using a multiplicity of infection (m.o.i.) of 5 pfu/cell. After three and a half hours 2, 5 ml DMEM supplemented with 20% FBS was added. The medium was exchanged the next day. After one more day, when extensive cytopathogenic effect (CPE) was observed, the cells were harvested. The cell suspension was centrifuged (200g, 10 minutes) and extrachromosomal DNA was isolated using a modified Hirt-extraction (Einerhand et al., 1995). Hirt-DNA was digested with 20 units DpnI (Biolabs, Leusden, The Netherlands) for 1 hour at 37° C. and size separated on agarose gels. DNA was Southern-blotted and filter hybridization was performed as described in (Maniatis et al., 1982). Filters were probed with a LacZ specific probe.

Production and Analysis of Ad/AAV Chimeric Viruses

Transfections were performed as described under "rescue and replication of minimal Ad/AAV chimeric constructs".

Two days after transfection the cells and the medium were harvested and subjected to lysis by three cycles of freeze-and-thaw (liquid N2/37° C.) to release the virus-particles into the culture medium. The supernatant was recovered after centrifugation (3000 g, 10 minutes) and filtered through a 0, 45 μm pore-sized nitrocellulose filter (Millipore, Etten-Leur).

Infections of Ad/AAV chimeric viruses were performed on HeLa. HeLa cells were seeded 106 cells per well (24 wells plate, Greiner). The next day 100 μl or 500 μl of supernatant was added. After 24 hours the cells were stained for LacZ activity.

To check for transfer of DNA packaged into adenovirus particles, 500 μl of filtered supernatant was treated with 100 μg/ml of DNaseI at 37° C. for 30 minutes, whereas another 500 μl of filtered supernatant was heated at 56° C. for one hour.

Cloning of Enlarged Ad/AAV Chimeric Molecules

Figure 6:
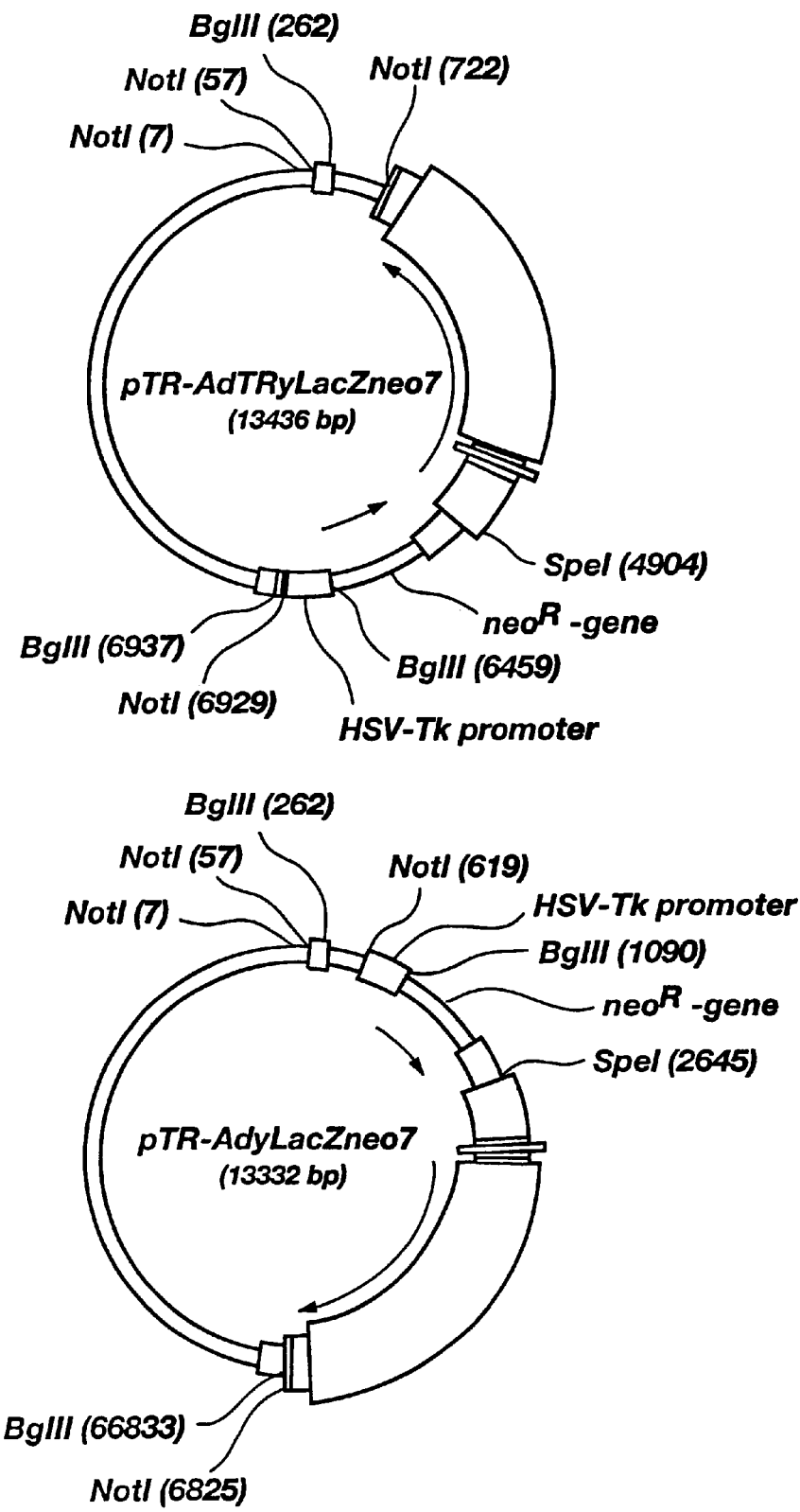
FIG. 6: Schematic representation of the cosmids pTR-AdTRyLacZneo7 and pTR-AdyLacZneo7. The number 7 indicates the expected size (in kb) of the rescued and replicated duplex monomer. These cosmids are derived respectively from the cosmids pTR⁺-AdTRyLacZ and pTR⁺-AdyLacZ by inserting, into a unique SpeI-site flanking the 5' end of the CMV-promoter, a $neo^R$-gene under transcriptional control of a herpes simplex virus (HSV) thymidine kinase (TK) promoter. Transcriptional orientation is depicted by arrows.
Figure 7A:
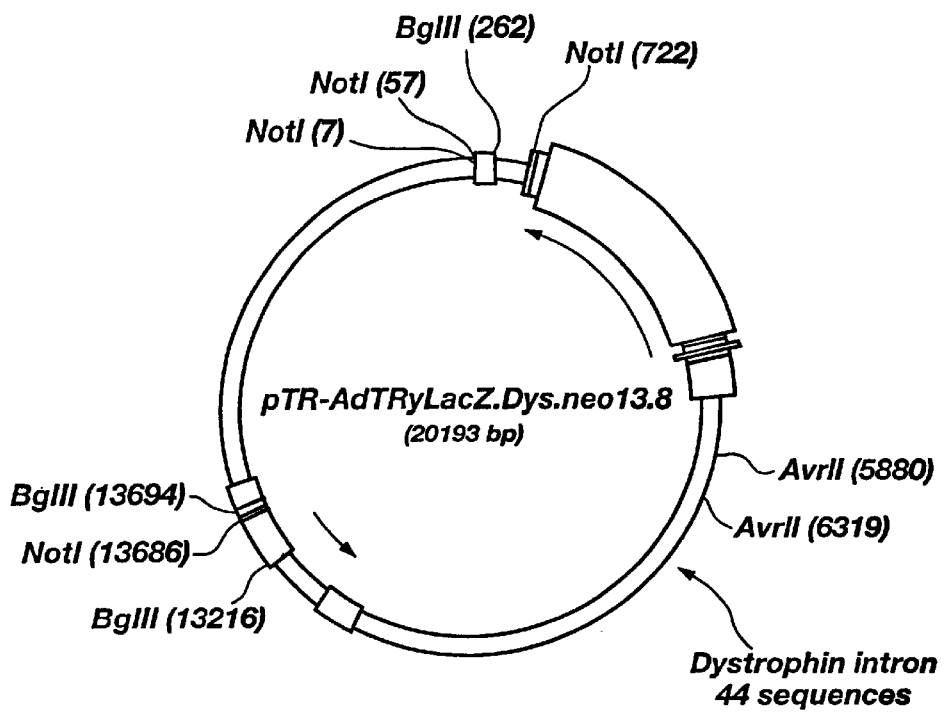
FIG. 7: Schematic representation of the cosmids pTR-AdTRyLacZ.Dys.neo13.8, pTR-AdyLacZ.Dys.neo14 (7A) and pTR-AdTRyLacZ.Dys.neo18 (7B). These are derived from the cosmids pTR-AdTRyLacZneo7 (pTR-AdTRyLacZ.Dys.neo13.8 & 18) or pTR-AdyLacZneo7 (pTR-AdyLacZ.Dys.neo14) by inserting into the SpeI site, fragments derived from the $44^{th}$ intron of the human dystrophin gene, as described in the text. The numbers 13.8, 14 and 18 indicate the expected size (in kb) of the rescued and replicated duplex monomers of the Ad/AAV chimeric molecules.
Figure 7A:
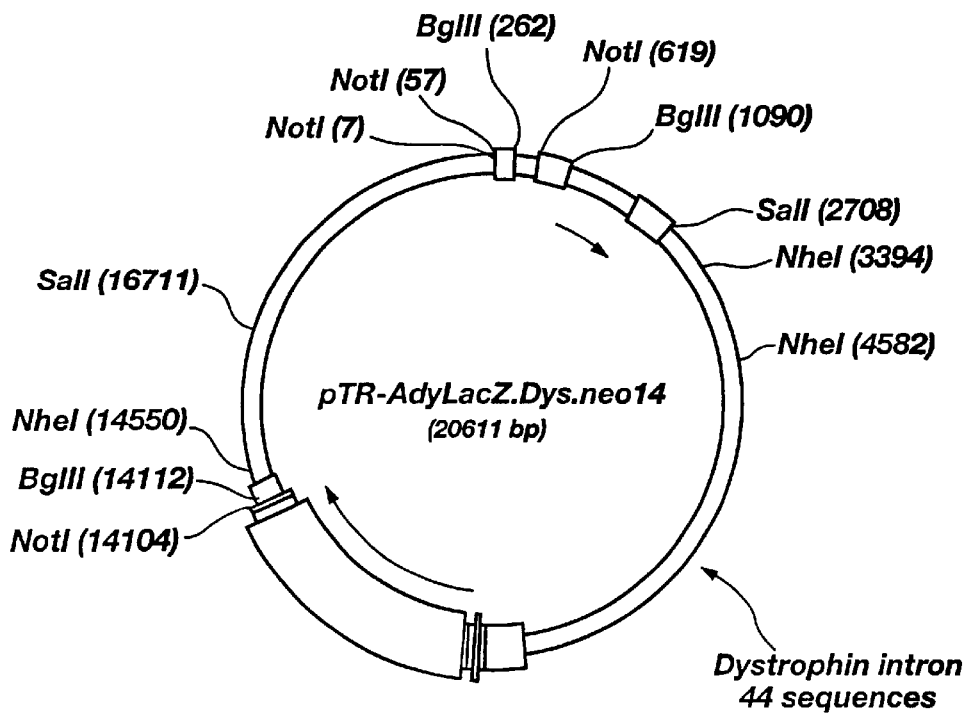
Figure 7B:
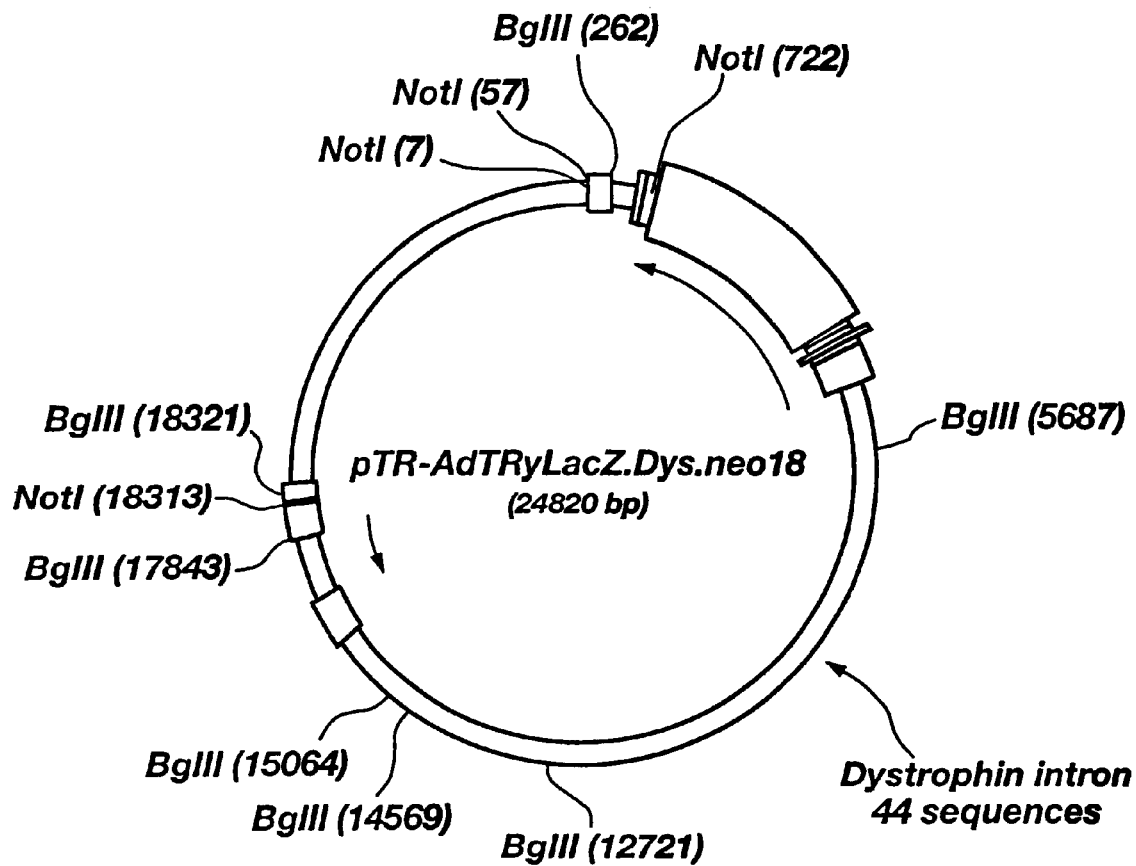

It is known that recombinant adenoviral genomes smaller than approximately 27 Kb have a strongly reduced packaging efficiency (Parks and Graham, 1997). Therefore, since we rely on Ad5-mediated packaging of the Ad/AAV replicons, we decided to increase the size of the Ad/AAV genome chimeras. The enlarged Ad/AAV chimeric molecules were created in two steps. First a neo$^R$-gene expression cassette was cloned into the cosmids pTR$^+$-AdΨLacZ and pTR$^+$-AdTRΨLacZ. Next different sized stuffer fragments obtained from the human dystrophin intron 44 were cloned into these cosmids. The neo$^R$-gene was cloned into the Spe I site flanking the 5' end of the CMV-promoter as a 2.0 kb Avr II-Spe I fragment from plasmid #221, resulting in the cosmids pTR-AdyLacZneo7 and pTR-AdTRyLacZneo7 (FIG. 6). The orientation of the neo$^R$-gene in the new cosmids was such that the restored Spe I site was directed towards the Lac Z expression cassette. Cloning of additional stuffer fragments into this Spe I site separates the LacZ and the neo$^R$-gene expression cassettes. Plasmid #221 was generated by ligating a 2.0 kb partial Nar I-fragment from plasmid 1417 (Talbot et al., 1989, Nature 338: 352–355) into the Cla I site of pBluescript SK$^-$ (Stratagene). Different sized Ad/AAV chimeric molecules were generated by inserting different sized stuffer fragments from the 44$^{th}$ intron of the human dystrophin gene (44Dys) (sequence can be obtained from GenBank Accession code: M86524). To generate pTR-AdTRyLacZ.Dys.neo.13.8, a 6.7 kb Nhe I-fragment from 44Dys was cloned into the Spe I site of pTR-AdTRyLacZneo7. To generate pTR-AdyLacZ.Dys.neo.14, a 7.3 kb Avr II-fragment from 44Dys was cloned into the Spe I site of pTR-AdyLacZneo7. To generate pTR-AdTRyLacZ.Dys.neo.18, a 11.4 kb Nhe I-fragment from 44Dys was cloned into the Spe I site of pTR-AdTRyLacZneo7. Finally, to generate pTR-AdTRy.33 and pTR-Ady.33, a 26.9 Kb Nae I-Pme I stuffer 44Dys DNA fragment was run on 1% Resolvase Low Melt Agarose (BioZym) and isolated using Agarase (Boehringer Mannheim). Manufacturer protocols were followed. This 26.9 Kb fragment was ligated to, respectively, Spe I digested, TSAP dephosphorylated and T4 DNA polymerase blunted pTR-AdTRyLacZneo7 and pTR-AdyLacZneo7. The two fragments were ligated with a final DNA concentration of 200 ng/ul using T4 DNA ligase. We followed the ligation/packaging protocol of the manufacturer of the lambda phage packaging extract (Stratagene). The ligated molecules were packaged into lambda phages which, in turn, were used to infect DH5α. (Gibco BRL, Life Technologies). Afterwards 800 μl of LB was added and the mixture was incubated for one hour at 37° C., 225 rpm. Subsequently, the bacteria were pelleted (3000 RPM, 5 min.) resuspended into 100 μl LB and plated onto LB plates containing 100 μg/ml ampicillin (Sigma). After overnight incubation at 37° C., colonies were picked and screened for the presence of insert-containing cosmids. For all cosmids containing dystrophin sequences, the junctions with the Ad/AAV chimeric vector were sequenced to verify identity and orientation of the dystrophin intron 44 derived sequences in the vector. For two of the constructs, characteristic restriction enzyme sites are depicted in FIGS. 7A and 7B.

Cloning of the Adenovirus Helper Constructs
pBR/Ad.Bam-rITR (ECACC Deposit P97082122)

In order to facilitate blunt end cloning of the ITR sequences, wild-type human adenovirus type 5 (Ad5) DNA was treated with Klenow enzyme in the presence of excess dNTPs. After inactivation of the Klenow enzyme and purification by phenol/chloroform extraction followed by ethanol precipitation, the DNA was digested with Bam HI. This DNA preparation was used without further purification in a ligation reaction with pBR322 derived vector DNA prepared as follows: pBR322 DNA was digested with Eco RV and Bam HI, dephosphorylated by treatment with TSAP enzyme (Life Technologies) and purified on LMP agarose gel (SeaPlaque GTG). After transformation into competent *E. coli* DH5a (Life Techn.) and analysis of ampicillin resistant colonies, one clone was selected that showed a digestion pattern as expected for an insert extending from the Bam HI site in Ad5 to the right ITR.

Sequence analysis of the cloning border at the right ITR revealed that the most 3' G residue of the ITR was missing, the remainder of the ITR was found to be correct.
pBr/Ad.Cla-Bam (ECACC Deposit P97082117)

wt Adeno type 5 DNA was digested with Cla I and Bar HI, and the 20.6 kb fragment was isolated from gel by electro-elution. pBR322 was digested with the same enzymes and purified from agarose gel by Geneclean. Both fragments were ligated and transformed into competent DH5α. The resulting clone pBr/Ad.Cla-Bam was analyzed by restriction enzyme digestion and shown to contain an insert with adenovirus sequences from bp 919 to bp 21566.
pBr/Ad.AflII-Bam (ECACC Deposit P97082114)

Clone pBr/Ad.Cla-Bam was linearized with EcoRI (in pBR322) and partially digested with AflII. After heat inactivation of Afl II for 20' at 65° C. the fragment ends were filled in with Klenow enzyme. The DNA was then ligated to a blunt double stranded oligo linker containing a Pac I site (5'-AATTGTC<u>TTAATTAA</u>CCGCTTAA-3' (SEQ. ID. NO.: 8)). This linker was made by annealing the following two oligonucleotides: 5'-AATTGTCTTAATTAACCGC-3' (SEQ. ID. NO.: 9) and 5'-AATTGCGGTTAATTAAGAC-3' (SEQ. ID. NO.: 10), followed by blunting with Klenow enzyme. After precipitation of the ligated DNA to change buffer, the ligations were digested with an excess Pac I enzyme to remove concatameres of the oligo. The 22016 bp partial fragment containing Ad5 sequences from bp 3534 up to 21566 and the vector sequences, was isolated in LMP agarose (SeaPlaque GTG), religated and transformed into competent DH5α. One clone that was found to contain the Pact site and that had retained the large adeno fragment was selected and sequenced at the 5' end to verify correct insertion of the Pac I linker in the (lost) Afl II site.
pBr/Ad.Bam-rITRpac#2 (ECACC Deposit P97082120) and pBr/Ad.Bam-rITR#8 (ECACC Deposit P97082121)

To allow insertion of a Pac I site near the ITR of Ad5 in clone pBr/Ad.Bam-rITR about 190 nucleotides were removed between the Cla I site in the pBR322 backbone and the start of the ITR sequences. This was done as-follows: pBr/Ad.Bam-rITR was digested with Cla I and treated with nuclease Bal31 for varying lengths of time (2', 5', 10' and 15'). The extend of nucleotide removal was followed by separate reactions on pBR322 DNA (also digested at the Cla I site), using identical buffers and conditions. Bal31 enzyme was inactivated by incubation at 75° C. for 10', the DNA was precipitated and resuspended in a smaller volume TE buffer. To ensure blunt ends, DNAs were further treated with T4 DNA polymerase in the presence of excess dNTPs. After digestion of the (control) pBR322 DNA with Sal I, satisfactory degradation (~150 bp) was observed in the samples treated for 10' or 15'. The 10' or 15' treated pBr/Ad.Bam-rITR samples were then ligated to the above described blunted Pac I linkers (See pBr/Ad.AflII-Bam). Ligations were purified by precipitation, digested with excess Pac I and separated from the linkers on an LMP agarose gel. After religation, DNAs were transformed into competent DH5α and colonies analyzed. Ten clones were selected that showed a deletion of approximately the desired length and these were further analyzed by T-track sequencing (T7 sequencing kit, Pharmacia Biotech). Two clones were found with the Pac I linker inserted just downstream of the rITR. After digestion with Pac I, clone #2 has 28 bp and clone #8 has 27 bp attached to the ITR.

pWE/Ad.AflII-rITR (ECACC Deposit P97082116)

Cosmid vector pWE15 (Clontech) was used to clone larger Ad5 inserts. First, a linker containing a unique Pac I site was inserted in the EcoRI sites of pWE15 creating pWE15.Pac. To this end, the double stranded Pac I oligo as described for pBr/Ad.AflII-Bam was used but now with its Eco R I protruding ends. The following fragments were then isolated by electro-elution from agarose gel: pWE15.Pac digested with PacI, pBr/Ad.AflII-Bam digested with Pac I and BamH I and pBr/Ad.Bam-rITR#2 digested with BamH I and Pac I. These fragments were ligated together and packaged using λ phage packaging extracts (Stratagene) according to the manufacturer's protocol. After infection into host bacteria, colonies were grown on plates and analyzed for presence of the complete insert. pWE/Ad.AflII-rITR contains all adenovirus type 5 sequences from bp 3534 (Afl II site) up to and including the right ITR (missing the most 3' G residue).

pWE/Ad.Δ5'

The construct pWE/Ad.Δ5' is an example of a replicating molecule according to the invention that contains two adenoviral ITRs and all adenoviral sequences between bp 3510 and 35938, i.e., the complete adenoviral genome except for the E1 region and the packaging signal. pWE/Ad.Δ5' has been made in a cosmid vector background from three fragments. First, the 5' ITR from Ad5 was amplified using the following primers: ITR-EPH: 5'-CGG-AAT-TCT-TAA-TTA-AGT-TAA-CAT-CAT-CAA-TAA-TAT-ACC-3' (SEQ. ID. NO.: 11) and ITR-pIX: 5'-ACG-GCG-CGC-CTT-AAG-CCA-CGC-CCA-CAC-ATT-TCA-GTA-CGT-ACT-AGT-CTA-CGT-CAC-CCG-CCC-CGT-TCC-3' (SEQ. ID. NO.: 12). The resulting PCR fragment was digested with EcoR I and Asc I and cloned into vector pNEB193 (New England Biolabs) digested with the same enzymes. The resulting construct was named pNEB/ITR-pIX. Sequencing confirmed correct amplification of the Ad5 sequences in the left ITR (Ad5 sequences 1 to 103) linked to the pIX promoter (Ad5 sequences 3511 to 3538) except for a single mismatch with the expected sequence according to GenBank (Accession no.: M73260/M29978), i.e., an extra G-residue was found just upstream of the Afl II site. This ITR-pIX fragment was then isolated with EcoR I and Afl II and ligated to a EcoR I-Afl II vector fragment containing Ad5 sequences 3539–21567. The latter fragment was obtained by digestion of pBr/Ad.Cla-Bam (supra) with EcoRI and partially with Afl II. The resulting clone was named pAd/LITR (Δ5')-BamH I. The final construct pWE/Ad.Δ5' was then made by ligating cosmid vector pWE15.Pac (supra) digested with Pac I to pAd/LITR(Δ5')-BamH I digested with Pac I/BamH I and pBr/Ad.Bam-rITR.pac#2 (supra) digested with Pac I/BamH I.

pWE/AAV-TR.Δ5'

The construct pWE/AAV-Tr.Δ5' is an example of a replicating molecule according to the invention that contains two AAV-ITRs, two adenovirus ITR and all adenoviral sequences between bp 3510 and 35938, i.e., the complete adenoviral genome except for the E1 region and the packaging signal. pWE/AAV-Tr.Δ5' has been made in a cosmid vector background from Pac I fragment from pWE/Ad.Δ5'. pWE/Ad.Δ5' was digested with Pac I, blunted with T4-polymerase, run on LMP-agarose (SeaPlaque GTG) and the 33 kb band was isolated using the Agarase™ (Boehringer Mannheim) according to the protocol of the manufacturer. Next pAAV-TR was digested with Bgl II, blunted with Klenow, dephosphorylated with TSAP (Life Technologies), run on LMP-agarose (SeaPlaque) and the 6 kb fragment containing the cosmid backbone and the AAV-TR was isolated with Agarase (Boehringer Mannheim). The two fragments were ligated with a final concentration of DNA of 200 ng/ul using T4-ligase and the ligation protocol of the lambda phage packaging extract manufacturer (Stratagene, Heidelberg, GE). The ligated molecules were packaged into lambda phages and infected into DH5a (Life Technologies) according to the protocol supplied by the lambda phage packaging extract manufacturer (Stratagene, Heidelberg, GE). Afterwards 800 ul of LB was added and the mixture was incubated for one hour at 37° C. Subsequently the bacteria were pelleted (3000 RPM, 5 min.), resuspended into 100 ul LB and plated onto LB plated containing 100 ug/ml ampicillin (Sigma). After overnight incubation at 37° C., colonies were picked and analyzed for the presence of insert containing cosmids.

cTr+LacZ

This molecule contains between AAV-TR a nuclear targeted LacZ driven by a CMV-promoter/enhancer and resembles the 5 kb Ad/AAV chimeric molecules but does not contain adenovirus sequences. cTR+LacZ was generated by cloning two fragments. pTR-AdTRyLacZ was digested with Bgl II, blunted with Klenow, dephosphorylated with TSAP (Life Technologies), run on LMP-agarose (SeaPlaque) and the 6 kb fragment containing the cosmid backbone and the AAV-TR was isolated with Agarase (Boehringer Mannheim). Next pTR-AdTRyLacZ was digested with Bgl II and Not I, blunted with Klenow, run on LMP-agarose (SeaPlaque) and the 4 kb fragment containing the CMV-LacZ expression cassette was isolated with Agarase (Boehringer Mannheim). The fragments were ligated and transformed into bacteria using general protocols (Maniatis et al., 1982).

Results

Biological Functionality of PCR Amplified CMV LacZ

The CMV-LacZ expression cassette in the minimal Ad/AAV chimeric constructs was derived from a PCR product. To verify the function of the expression cassette the intermediate clones pAdyLacZ, pAdTRyLacZ and pD18AdTR y LacZ were transfected into PER.C6 cells and after 48 hours stained with X-Gal for LacZ activity.

The LacZ expression cassette was intact in all constructs (Table 1). Interestingly, the increase in the number of blue cells follows the increase in the length of Ad5 sequences present in the constructs.

Minimal Ad/AAV chimeric constructs are rescued and replicated in permissive cells in the presence of Rep.

In the minimal Ad/AAV chimeric constructs described here, the sequence of interest is flanked by AAV-TR to facilitate integration of the vector into the target cell DNA. The fact that the AAV-TR form the extreme ends of the molecule has implications not only for the integration of the vector into the target cell genome but also for the multiplication of the vector in the vector producing cells. Multiplication of the Ad/AAV-vector through adenovirus early genes is not possible. However, Rep-mediated replication should be efficient. To test this assumption, we transfected the minimal Ad/AAV chimerical constructs either in the presence or absence of the rep-expression plasmid pDRBE-rep into the Ad5 E1 trans-complementing PER.C6 cell line (WO 97/00326). The cells were infected with an E1-deleted helper adenovirus (IG Ad CMV Luc) to supply the remaining trans required adenovirus functions. Two days after transfection, the cells were harvested and extrachromosomal DNA was isolated through Hirt-extraction. To verify rescue and eukaryotic replication of the Ad/AAV chimeric vectors the hirt-extract DNA was digested with the restriction enzyme DpnI. DpnI requires its overlapping DAM-site to be methylated for restriction. In normal DAM+E. Coli strains the DpnI-sites in plasmid DNA are methylated and thus sensitive to DpnI-digestion. Eukaryotic cells lack DAM activity. Newly formed DNA in eukaryotic cells will not be DAM-methylated and thus become resistant to DpnI-digestion whereas the transfected DNA retains its DAM-methylation pattern and is DpnI-sensitive.

Figure 4:
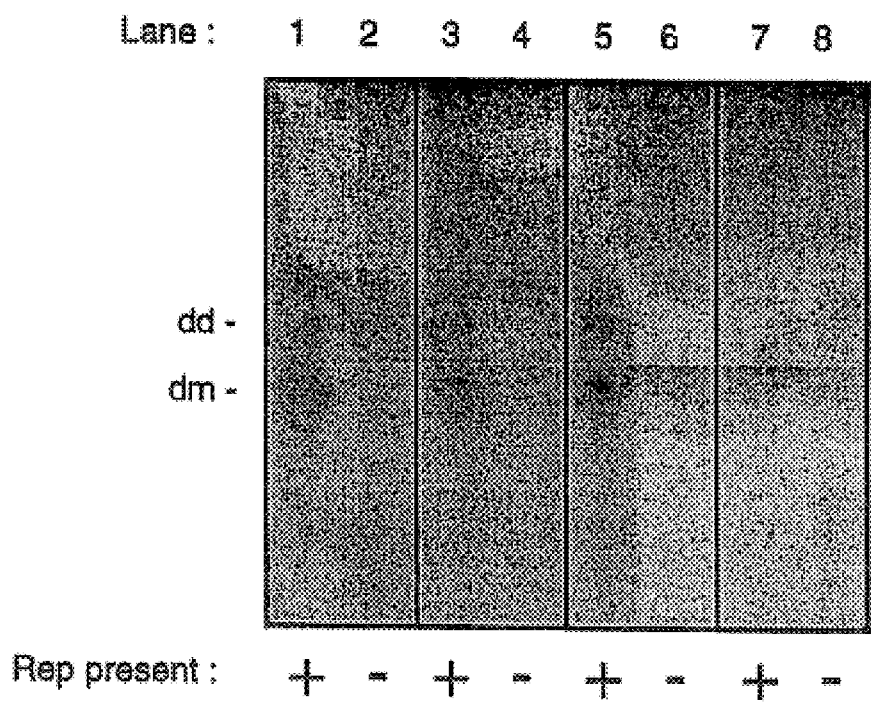
FIG. 4: Southern of Hirt-extract DNA from PER.C6 cells transfected with minimal Ad/AAV chimeric constructs. PER.C6 cells infected with IG Ad CMV Luc were transfected with minimal Ad/AAV chimeric constructs pTR⁺-AdyLacZ (lanes 1 and 2), pTR⁺-AdD18TRyLacZ (lanes 3 and 4), pTR⁺-AdTRyLacZ (lanes 5 and 6) or pTR⁺-AdTRyLacZ in which both AAV-TR contain rearrangements (lanes 7 and 8). Transfections were performed either in the presence (+) or absence (−) of the rep-expression plasmid pDRBErep. One day after transfection extrachromosomal DNA was isolated, digested with the restriction enzyme DpnI, Southern blotted and hybridized to a LacZ-specific probe. Bands corresponding to the size of the duplex monomer (dm) and duplex dimer (dd) are indicated.

The presence of the adenovirus TR and/or the adenovirus packaging signal does not interfere with Rep-mediated rescue and replication in permissive cells (FIG. 4, lanes 1, 3 and 5). All constructs are rescued and replicated efficiently. The size of the products correspond to the expected sizes for the duplex monomer and the duplex dimer. Replication is dependent on the presence of Rep. In the absence of Rep or when the TR-sequence is mutated no replication is observed (FIG. 4, lanes 2, 4, 6 and 8 or lane 7, respectively). From these results we conclude that the Ad/AAV chimeric molecules described here behave like recombinant AAV-molecules with respect to rescue from plasmid DNA and subsequent replication.

Figure 5:
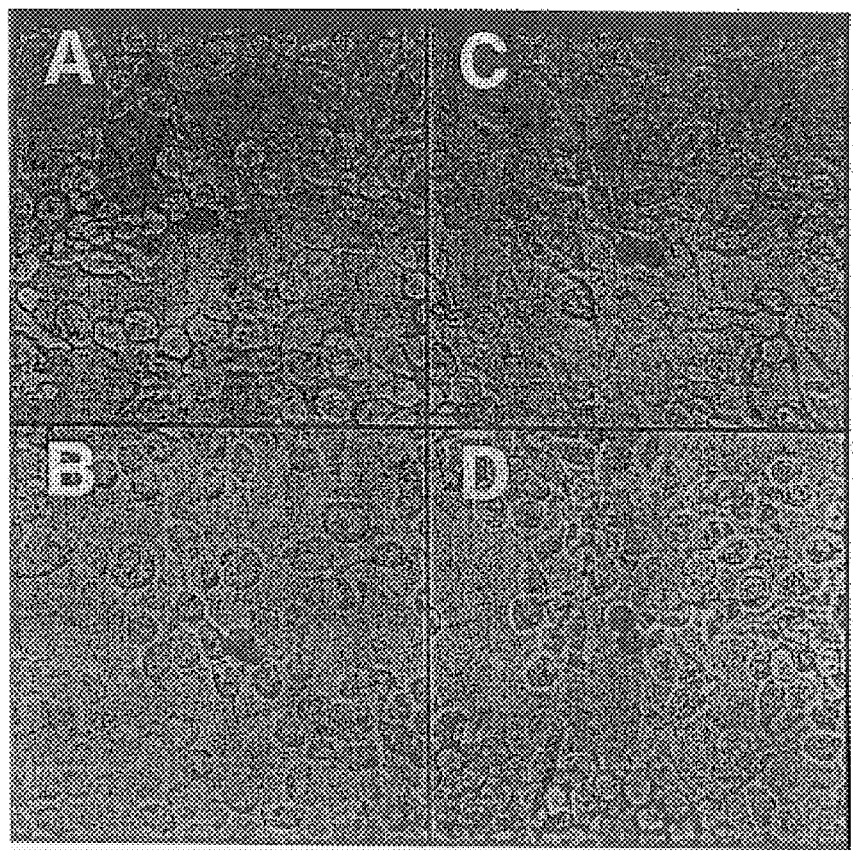
FIG. 5: Micrographs of HeLa cells stained with X-Gal 24 hours after infection with recombinant chimeric virus pTR⁺-AdTRyLacZ. Dark X-gal stained single cells are easily identified (panel A and B). Also detected daughter cells from a recent cell division, in which both cells are positive for beta-galactosidase activity (panel C and D).

Minimal Ad/AAV Chimeric Constructs are Packaged into Adenovirus 5 Capsids in Permissive Cells in the Presence of Rep Next, we wanted to know whether the Ad/AAV chimeric molecules are packaged into adenovirus capsids. It is known for recombinant adenovirus genomes that packaging of genome size (36 kb) vectors are preferentially packaged (Parks and Graham, 1997). Recombinant genomes smaller than 27 kb have a strongly reduced packaging efficiency. However, low efficient packaging of small genomes is possible and detectable (Parks and Graham, 1997). To verify whether the Ad/AAV chimeric molecules-of the present invention were packaged into adenovirus particles, we transfected the constructs into PER.C6 cells either in the presence or in the absence of a rep-gene containing construct. The cells were also infected with the E1-deleted helper adenovirus IG Ad CMV Luc. Virus was isolated after 48 hours, and the filtered supernatant was titrated on HeLa-cells. Blue cells were detected in all three chimeric viruses (Table 2). Blue cells were also detected when pTR-AdTRyLacZ virus pretreated with DNaseI but not when the virus was heat inactivated at 56° C. for 1 hour, implying that the DNA was transferred in completely closed adenovirus particles (not shown). Significant titratable virus was detected only when virus was produced in the presence of Rep (Table 2), indicating that replicated linear genomes are more efficiently packaged than circular DNA. The adenovirus packaging signal containing chimeric viruses are packaged irrespective of the presence of adenovirus TR sequences. However, the highest number of blue cells are detected with the chimeric virus containing the complete TR (Table 2). This result suggests that adenovirus TR-sequences are involved in the packaging of adenovirus genomes. However, it is very well possible that adenovirus TR sequences enhance expression of LacZ. Indications that this might occur come from data in Table 1, where transfection of the construct containing the entire adenovirus TR gave the highest number of blue cells. When cells were stained for LacZ activity, isolated stretched out blue cells are detected. Also detected are blue stained recently divided. Thus, LacZ expression is detected in both daughter cells from a recent cell division (FIG. 5), indicating integration of the vector into the DNA of the ancestor cell before division.

Replication of Enlarged Ad/AAV Chimeric Molecules

We studied the rescue and replication of the enlarged AAV replicon-containing molecules. PER.C6 cells were seeded with a density of $10^7$ cells per 100 mm dish (Greiner). The cells were transfected the next day with Lipofectamine according to the specification of the manufacturer using 120 μl lipofectamine and 24 μg of total DNA. When adenovirus vectors were used to provide helper function for AAV-mediated replication, the cells were infected with IG Ad CMV Luc (2.5 pfu/cell) at the time of transfection. The ratio of Ad/AAV vector chimera to pΔRBErep was 1 to 4 (w/w). When helper functions were provided by transfection of the cosmid helper vector pWE/Ad.Δ5', the ratio of the cosmids and plasmids in the transfection mixture was 1:4:4 (w/w/w) for, respectively, the Ad/AAV chimeric molecule, pDRBErep also referred to as pΔRBErep, and pWE/Ad.Δ5'. Prior to transfection, the pWE/Ad.Δ5' was digested with Pac I (Biolabs) to free the adenovirus terminal repeat elements from the cosmid DNA vector. The PER.C6 cells were cultured for 48 hours before Hirt-extraction. Hirt-DNA was digested with 20 units Dpn I (Biolabs) for 1 hour at 37° C. and size separated on 0.3% high gel strength SeaKem gold agarose (FMC Bioproducts, Rockland Me., USA). DNA was Southern blotted (Maniatis et al., 1982) and hybridized with a LacZ $^{32}$ p labeled DNA fragment (RTS labeling system, Gibco BRL, Life Technologies).

Figure 8:
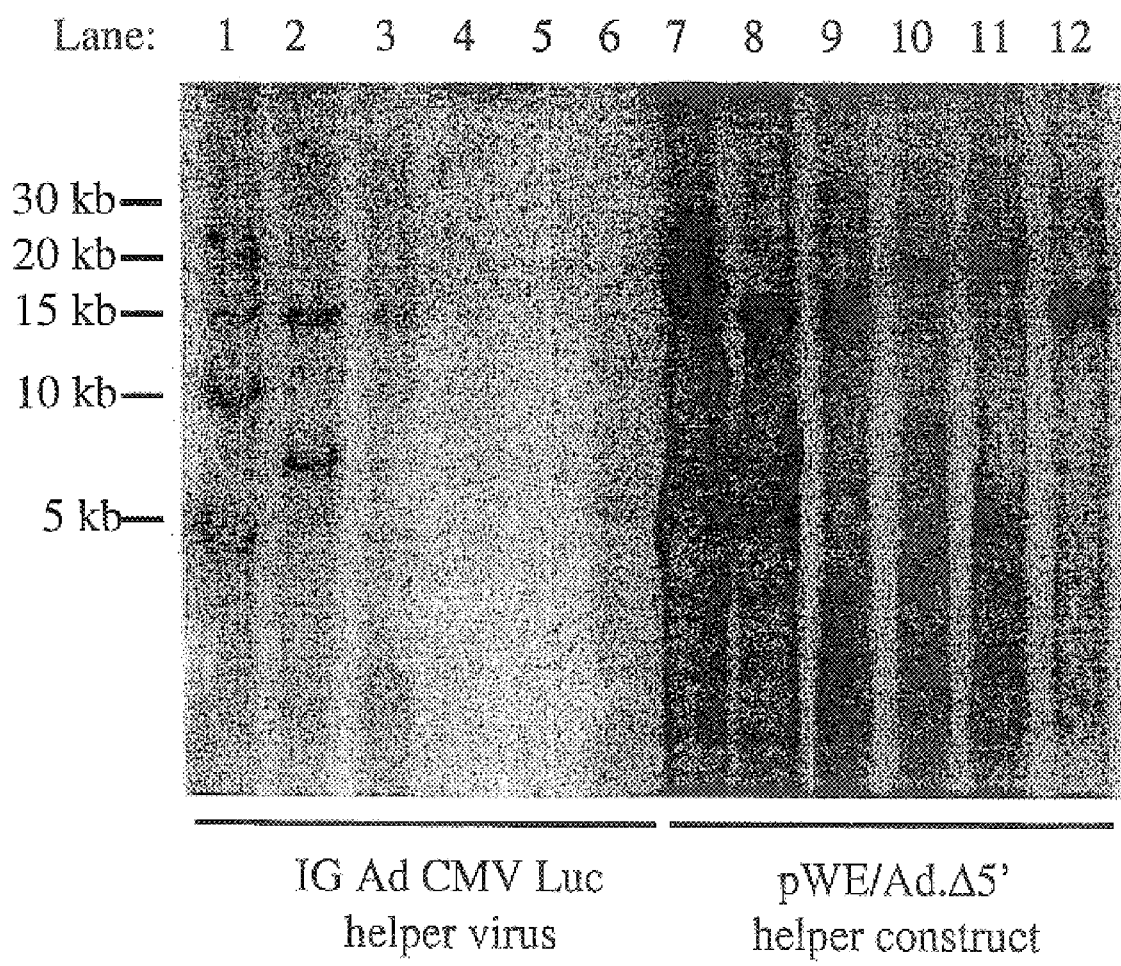
FIG. 8. Southern blot of Hirt-extracted DNA from PER.C6 cells transfected with Ad/AAV chimeric molecules and the rep-expression plasmid pAREBrep. PER.C6 cells were either infected with IG Ad CMV Luc (2.5 pfu/cell, lanes 1 to 6) or transfected with pWE/Ad.Δ5' (lanes 7 to 12). Lanes 1 and 7: PER.C6 cells transfected with pTR-AdTRyLacZ. Lanes 2 and 8: PER.C6 cells transfected with pTR-AdTRyLacZneo7. Lanes 3 and 9: PER.C6 cells transfected with pTR-AdyLacZ.Dys.neo14. Lanes 4, 5, 10 and 11: PER.C6 cells transfected with pTR-AdTRyLacZ.Dys.neo18. Lanes 6 and 12: PER.C6 cells transfected with pTR-AdTRyLacZ.Dys.neo13.8. The size indication on the left hand of the Figure is derived from molecular size markers lambda×HindIII×EcoRI and High molecular weight DNA markers (Life Technologies, Breda, The Netherlands).

In the presence of adenovirus vector IG Ad CMV Luc, replication of 5 and 7 kb Ad/AAV chimeric molecules is easily detectable (FIG. 8, lanes 1 and 2). However, the Ad/AAV chimeric molecules of 13.8, 14 and 18 kb length were not detectable, indicating severely impaired replication characteristics (FIG. 8, lanes 3 to 6). When pWE/Ad.Δ5' was used to provide the helper functions, replication of the 5 and 7 kb molecules is more efficient than in the presence of adenovirus vector IG Ad CMV Luc (FIG. 8, compare lanes 1 an d 2 with lanes 7 and 8). In addition, replication of the 13.8, 14 and 18 kb Ad/AAV chimreric molecules is easily detectable (FIG. 8, lanes 9 to 12). Thus, efficient replication of Ad/AAV chimeric molecules up to at least 18 kb is attainable.

In the experiment described above, replication of enlarged Ad/AAV chimeric molecules is detected in the absence of adenovirus vectors, suggesting competition between the replication of the adenovirus vector and the Ad/AAV chimeric molecule. Competition can be either for a cellular factor(s) for helper functions provided by adenovirus genes, or both. To study this we performed the following experiment.

Figure 9:
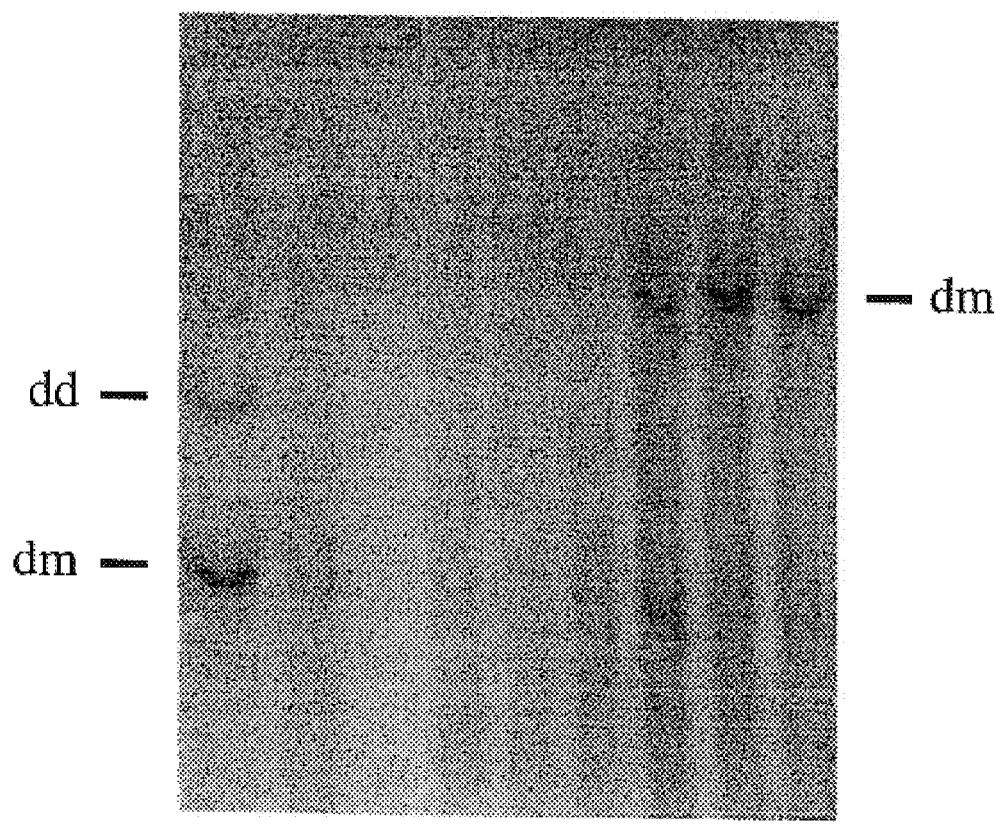
FIG. 9: Southern blot of Hirt-extracted DNA from PER.C6 cells transfected with Ad/AAV chimeric molecules and the rep-expression plasmid pΔRBErep. PER.C6 cells were infected with IG Ad CMV Luc (20 pfu/cell). PER.C6 cells were transfected with pTR-AdTRyLacZ (lane 1) or with pTR-AdTRyLacZ.Dys.neo18 (lanes 2,4–9). Lane 3 contains the high molecular weight DNA markers (Life Technologies, Breda, The Netherlands). The effect of extra dNTP (Life Technologies, Breda, The Netherlands) on the rescue and replication of pTR-AdTRyLacZ.Dys.neo18 was studied through the addition of 300 uM, 30 uM or 3 uM dNTP to the medium following transfection, lanes 4, 5 and 6 respectively. The effect of extra E2a protein was studied by co-transfecting, 2.5 ugram, 7.5 and 12.5 ugram plasmid pcDNA3.CMVwtE2A, lanes 7, 8 and 9 respectively. The position of the duplex monomers (dm) and duplex dimers (dd) are indicated.

PER.C6 cells were seeded at a density of $10^7$ per 100 mm dish (Greiner). The next day the cells were cotransfected with pTR-AdTRyLacZ or pTR-AdTRyLacZ.Dys.neo18 plus pΔRBErep (ratio 1:4 w/w) and, at the same time, infected with IG Ad CMV Luc (20 pfu/cell). To three different samples was added extra dNTPs to the medium, whereas, three other samples received increasing amounts of an expression plasmid pcDNA3.CMVwtE2A encoding the adenovirus-5 E2A gene. Once again, Hirt-extracted DNA was isolated after 48 hours and 20 units Dpn I (Biolabs) digested for 1 hour at 37° C. The fragments were size separated on 0.3% high gel strength SeaKem gold agarose (FMC Bioproducts, Rockland Me., USA). DNA was Southern blotted (Maniatis et al., 1982) and hybridized with a LacZ $^{32}$ p labeled DNA fragment (RTS labeling system, Gibco BRL, Life Technologies). Again, replication of a 5 kb Ad/AAV genome chimera is easily detectable whereas replication of pTR-AdTRyLacZ.Dys.neo.18 is not (FIG. 9, lanes 1 and 2). Extra dNTPs added to the medium do not influence the replication of pTR-AdTRyLacZ.Dys.neo.18 in a detectable fashion (FIG. 9, lanes 4 to 6). However, when the expression plasmid containing the adenovirus 5 a CMV driven E2a was added during transfection, replication of pTR-AdTRyLacZ.Dys.neo.18 is clearly observed (FIG. 9, lanes 7 to 9).

Concentration/purification of Ad/AAV Chimeric Vectors by CsCl Density Gradients

We purified Ad/AAV chimeric virus particles by CsCl density gradients. A small scale production of a 13.8 Kb genome size Ad/AAV chimeric vector was produced as follows. Five 100 mm petri dishes (Greiner) were seeded with a density of $1 \times 10^7$ PER.C6 cells per dish. Cells were incubated at 37° C. in DMEM (Gibco BRL, Life Technologies) with 10% FBS (Gibco BRL, Life Technologies) and 10 mM MgCl$_2$ (Sigma). The next day the cells were transfected with Lipofectamine according to the specification of the manufacturer using 100 µg Lipofectamine and 24 µg of total DNA. This total amount of DNA consisted of pTR-AdTRyLacZ.Dys.neo.13.8 (3.6 µg), pΔRBErep (8.0 µg), pcDNA3.CMVwtE2A (5 µg) and pWE/Ad.AflII-rITR (8 µg). After overnight incubation at 37° C. in a 10% CO$_2$ atmosphere, fresh medium (DMEM, 10% FBS, 10 mM MgCl$_2$) was added onto the transfected cells. Approximately 48 hours post-transfection, cells were infected with the adenoviral vector IG.Ad.MLP Luc at a m.o.i. of 5 p.f.u./cell. Three days post-infection, cytophatic effect (CPE) was complete. The cells were harvested, and the cell suspension (50 ml) was centrifuged for 15 minutes at 2000 rpm. The cellular pellet was washed by adding PBS (NPBI) followed by resuspension and centrifugation (15 minutes, 2000 rpm). The washed pellet was resuspended in 1 ml of lysis buffer (NaPO$_4$ 10 mM) with 10% glycerol and subjected to three cycles of freezing (liquid N$_2$) and thawing (37° C.). Afterwards MgCl$_2$ and DNAse I were added with final concentrations of, respectively, 32 mM and 6000 u/ml. Mixture contents were homogenized by gentle inversion. Incubation for 30 minutes at 37° C. followed, after which, the sample was centrifuged at 2000 rpm for 20 minutes. The supernatant was recovered and freon extracted by addition of one volume of freon and homogenization by gentle inversion. The two phases were resolved by centrifugation at 2000 rpm for 5 minutes. The upper fraction was recovered without any interface and laid onto a CsCl block gradient comprised of the following three density tiers; 1.25, 1.35 and 1.5 g/ml. Ultracentrifugation was performed with a SW 60 rotor (Beckman) in a Beckman L8-M ultracentrifuge at 10° C. for 3 hours at 25,000 rpm. Fractions were collected dropwise by puncturing with a needle the bottom of the centrifuge tube. The presence of LacZ-transducing units (blue forming units—BFUS) corresponding to the packaged, DNAse I resistant, 13.8 Kb Ad/AAV chimeric genome were evaluated by infecting $5 \times 10^5$ HeLa cells in 6 well plates (Greiner) with 10 µl of each fraction. Twenty four hours later infected cells were subjected to the β-Gal staining assay (see "E. coli β-Galactosidase activity staining"). After overnight staining at 37° C. blue cells were counted under an optical microscope (Olympus CK2-TR). On the other hand, the presence of the IG.Ad.MLP Luc helper vector was determined by infecting $5 \times 10^5$ HeLa cells in 6 well plates (Greiner) with 2 µl of each fraction. Twenty four hours post-infection HeLa cells were harvested and resuspended in 2 ml PBS (NPBI). Afterwards the suspension was centrifuged at 2000 rpm for 10 minutes and the cell pellets were lysed and assayed for luciferase activity. Manufacturer protocol was followed (Promega). Table 3 summarizes the results from representative fractions for these two assays.

Fractions numbers 11, 12, 13 and 14 (see Table 3) from the CsCl block gradient were pooled and laid onto a 1.32 g/ml CsCl solution in a Quick-Seal (13×51 mm) centrifuge tube (Beckman). Ultracentrifugation was performed overnight at 10° C. in an Optima TLX ultracentrifuge at 73,000 rpm. Once again, fractions were collected dropwise by puncturing with a needle the bottom of the centrifuge tube. Furthermore using Centricon-100 cartridges (Amicon Bioseparations), and according to manufacturer instructions, fractions were CsCl desalted by two successive rounds of PBS dilution followed by sample concentration throughout centrifugation. The presence of BFUs in the CsCl desalted fractions was evaluated by infecting $5 \times 10^5$ HeLa cells in 6 well plates (Greiner) with 20 µl of each fraction. Twenty four hours later infected cells were subjected to the β-Gal staining assay (see "E. coli β-Galactosidase activity staining"). After overnight staining at 37° C. blue cells were counted under an optical microscope (Olympus CK2-TR). The presence of the IG.Ad.MLP Luc. helper vector was, once again, determined by infecting $5 \times 10^5$ HeLa cells in 6 well plates (Greiner) with 2 µl of each fraction. Twenty four hours post-infection, HeLa cells were harvested and resuspended in 2 ml PBS (NPBI). Afterwards, the suspension was centrifuged at 2000 rpm for 10 minutes and the cell pellets were lysed and assayed for luciferase activity. Manufacturer protocol was followed (Promega). Table 4 summarizes the results from representative fractions for these two assays.

From the data depicted on Table 3 we can conclude that Ad/AAV chimeric vectors are amenable to CsCl ultracentrifugation. Furthermore, the data presented on Table 4 clearly shows that using a CsCl continuous gradient a packaged Ad/AAV chimeric genome of 13.8 Kb can be partially resolved from a ΔE1 helper adenoviral vector. With proper optimization (e.g., CsCl solution density, fraction recovering), higher resolution between the two vectors should be attainable.

Optimization of Ad/AAV Chimeric Vector Production
Dependence on Adenovirus Terminal Repeat and Packaging Sequences, also Referred to as AdTRΨ, or AdTRy We designed an experiment to further determine the involvement of the adenovirus serotype-5 left TR in the packaging process of rescue/replicated Ad/AAV chimeric genomes. Therefore, $1 \times 10^7$ PER.C6 cells were seeded on 100 mm dishes (Greiner) and, the following day, transfected with 18 μg total DNA using 100 μl of Lipofectamine (Gibco BRL, Life Technologies). Furthermore, transfection was made according to manufacturer instructions. The DNA mixture consisted of either cTr+LacZ, pTR+-AdyLacZ or pTR+-AdTRyLacZ with pΔRBErep (1:3 [w/w], respectively) and pUC19 as carrier DNA. During transfection, the structural adenovirus proteins were provided by IG.Ad.MLP Luc infection (m.o.i. 5). After complete CPE, cells were harvested, three times freeze ($N_2$)/thawed (37° C.). The cell debris were pelleted by brief centrifugation, and 0.5 ml of each supernatant was used to infect $5 \times 10^5$ HeLa cells. The presence of BFUs was assayed by the β-Gal staining assay (see "E. Coli β-Galactosidase activity staining"). Blue cells were counted under an optimal microscope (Olympus CK2-TR).

Supernatants derived from cTR+LacZ, pTR+-AdΨLacZ (also referred to as pTR+-AdyLacZ) and. pTR+-AdTRΨLacZ (also referred to as pTR+-AdTRyLacZ) transfected PER.C6 cells gave rise to 49, 35 and 751 BFUs, respectively. After heat-treatment (56° C., 1 hour) of all the above mentioned samples, no blue cells were detected.

This data indicates that the adenovirus serotype-5 TR is involved in the packaging of replicated Ad/AAV chimeric genomes. Therefore, further experiments concerning the optimization of the Ad/AAV production system were focused in TR-containing constructs.

Rescue-replication of Enlarged Ad/AAV Chimeric Genomes Prior to ΔE1-helper Vector Infection Enhances Packaging Previous data showed that enlarged Ad/AAV chimeric genomes replicated only without the presence of the ΔE1 helper adenoviral vector. Consequently, the formation of chimeric vectors with larger genomes is highly hampered under the conditions where the helper viral vector is present since the time of transfection. Therefore, we decided to test whether we could observe enhanced packaging by infecting the cells 48 hours post-transfection and, by that way, enhance the accumulation of replicated Ad/AAV chimeric genomes. PER.C6 cells were seeded with a density of $1 \times 10^7$ cells per 100 mm dishes (Greiner). The next day the cells were co-transfected either with pTR+-AdTRΨLacZ (1.5 μg), pTR-AdTRyLacZ.Dys.neo.13.8 (3.6 μg) or pTR-AdTRy.33 (8 μg) and pΔRBErep (5 μg), pcDNA3.CMVwtE2A (5 μg) and pWE/Ad.AflII-rITR (8 μg). One hundred μl Lipofectamine (Gibco BRL, Life Technologies) was used per transfection mixture and manufacturer instructions were followed. After overnight incubation at 37° C. in an atmosphere with 10% $CO_2$, the transfection medium was replaced with freshly added medium (DMEM, 10% FBS, 10 mM $MgCl_2$). After 48 hours post-transfection, the cells were infected with IG.Ad.MLP.Luc helper vector. In other experimental setting, the same transfection conditions were used, but the helper infection was made at the time of transfection. After complete CPE, the cells were harvested, three times freeze ($N_2$) and thawed (37° C.), and the supernatants were recovered after a brief centrifugation. The Ad/AAV chimeric vectors were titrated on HeLa cells as above described. Crude lysates derived from pTR+-AdTRΨLacZ (Ad/AAV 5 Kb), pTR-AdTRyLacZ.Dys.neo.13.8 (Ad/AAV 13.8 Kb) and pTR-AdTRy.33 (Ad/AAV 33 Kb) contained titers of $0.7 \times 10^3$, $4 \times 10^3$ and $0.2 \times 10^3$ BFU/ml, respectively. When using the same constructs and experimental conditions, but with the helper vector infection being at the moment of transfection, the amounts of BFUs rescued were, respectively, $0.6 \times 10^3$, $0.2 \times 10^3$ and non detectable. These results show that for the enlarged Ad/AAV genomes, prior to packaging, replication in the absence of competing helper vector is necessary for the enhanced packaging ability. These results, once again (see "Minimal Ad/AAV chimeric constructs are packaged into adenovirus 5 capsids in permissive cells in the presence of Rep"), directly relate rescue-replication ability with packaging competence.

Propagation of Ad/AAV Chimeric Vectors on Rep/E2A-transfected PER.C6 Cells

In search for methods that would enable us to further increase the Ad/AAV chimeric vector titers, we decided to investigate whether the produced chimeric vectors were able to propagate on permissive cells. Before the addition of Ad/AAV-containing crude lysates, PER.C6 cells were co-transfected with the Rep and E2A-containing expression plasmids.

PER.C6 cells were seeded with a density of $1 \times 10^7$ cells per 100 mm dishes (Greiner). One hundred μl Lipofectamine (Gibco BRL, Life Technologies) was used per transfection mixture, and manufacturer instructions were followed. The next day the cells were co-transfected with 5 μg of either pΔRBErep or pUC19 and 7 μg of pcDNA3.CMVwtE2A. After overnight incubation at 37° C. in an atmosphere with 10% $CO_2$, the transfection medium was replaced with freshly added medium (DMEM, 10% FBS, 10 mM $MgCl_2$) and, at the same time, 200 μl of either Ad/AAV 5 Kb (140 BFUs) or Ad/AAV 13.8 Kb (800 BFUs) chimeric vector-containing crude lysate were added (see section above). The presence of ΔE1-helper vector led to CPE on the transfected cells. The crude lysates were titrated on HeLa cells as above described. The ratio of total rescued (8230 BFUs) to inputted (800 BFUs) LacZ-transducing units for the Ad/AAV 13.8 Kb chimeric vector was 10. Whereas, for the Ad/AAV 5 Kb chimeric vector, the ratio of total rescued (855 BFUs) to inputted (140 BFUs) LacZ-transducing units was 6. Blue cells were not detected when the infection with the Ad/AAV-containing crude lysates were performed in pUC19/pcDNA3 .CMVwtE2A co-transfected PER.C6 cells. This indicates that chimeric vector propagation is dependent on the presence of AAV Rep proteins. Therefore, the packaged genomes retain functional ITRs. Since AAV ITRs are the only required substrate for integration, we can conclude that the Ad/AAV chimeric vectors retain the integration ability of AAV-based vectors.

Time-course of Accumulation of AAV-mediated Replication Forms

With this next experiment we wanted to, once again, address the replication ability of Ad/AAV chimeric replicons above wild-type AAV genome size (i.e. above approximately 5 Kb). We have shown that the adenovirus type-5 E2A gene product when supplied by transient transfection of an expression plasmid enhances the rescue/replication of all the AAV-replicon containing constructs (see "Replication of enlarged Ad/AAV chimeric molecules"). However, replication of the enlarged Ad/AAV chimeric genomes decreases with the increase in their size. Therefore, with this next experiment we wanted to know whether there was a time dependency on the accumulation of AAV-mediated replication forms (Rfs) corresponding to the enlarged Ad/AAV chimeric genomes and, at the same time, we wanted to evaluate the ability of a 33 Kb Ad/AAV genome to be rescued and replicated from its cosmid backbone.

Figure 10:
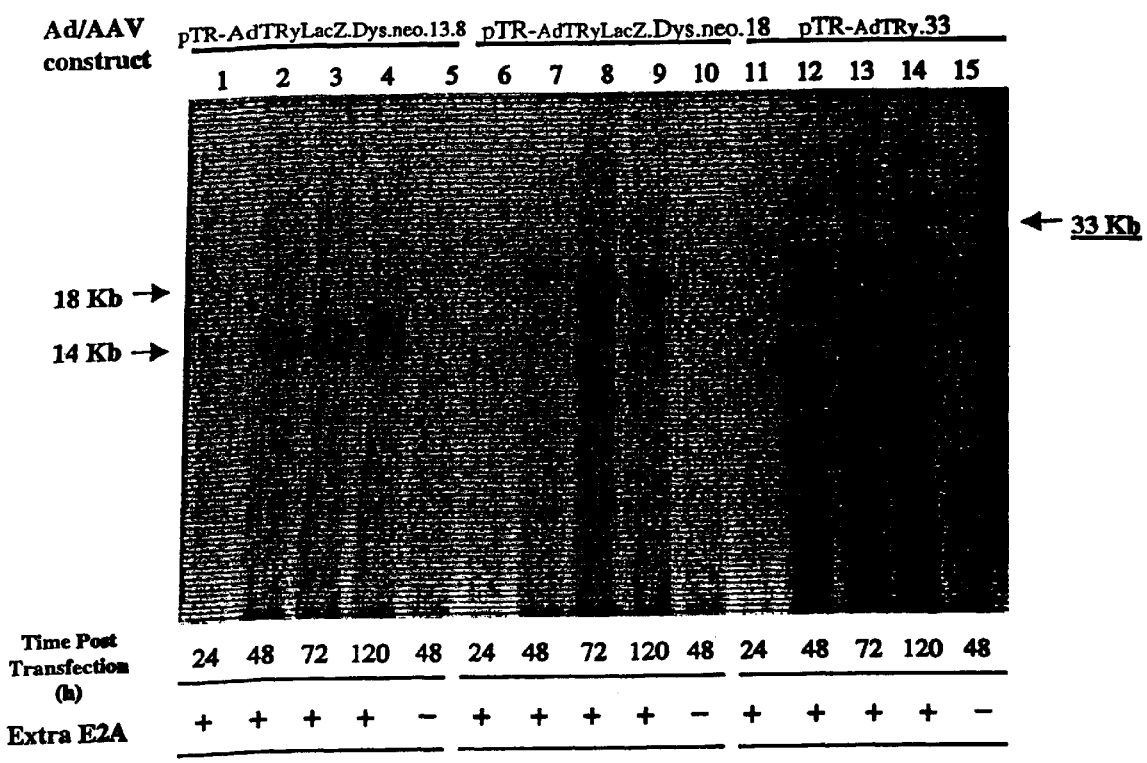
FIG. 10: Time course of Ad/AAV genome replication. Southern blot of Hirt-extracted DNA from PER.C6 cells co-transfected with Ad/AAV chimeric constructs, rep-expression plasmid pΔRBErep, E2A-expression plasmid pcDNA3.CMVwtE2A and pWE/Ad.AflII-rITR (pTR-AdTRyLacZ.Dys.neo.13.8: lanes 1–4, pTR-AdTRyLacZ.Dys.neo.18: lanes 6–9 and pTR-AdTRy.33: lanes 11–14). Time points corresponding to the number of hours post-transfection, after which samples were harvested, are indicated below. PER.C6 cells co-transfected with Ad/AAV chimeric constructs, rep-expression plasmid pΔRBErep and pWE/Ad.AflII-rITR (pTR-AdTRyLacZ.Dys.neo.13.8: lane 5, pTR-AdTRyLacZ.Dys.neo.18: lane 10, pTR-AdTRy.33: lane 15). PER.C6 cells that were not transfected with pcDNA3.CMVwtE2A were harvested at 48 hours post-transfection.

One basic transfection scheme was carried out as follows. PER.C6 cells were seeded with a density of $4 \times 10^6$ cells per T25 flask (Nunc). The next day, approximate equimolar amounts of the constructs pTR-AdTRyLacZ.Dys.neo.13.8 (2 μg), pTR-AdTRyLacZ.Dys.neo.18 (2.5 μg) and pTR-AdTRy.33 (4 μg) were co-transfected with pΔRBErep (2 μg), pcDNA3.CMVwtE2A (2 μg) and pWE/Ad.AflII-rITR (5 μg). In other experimental settings, each of the above mentioned Ad/AAV chimeric constructs were co-transfected only with pΔRBErep (2 μg) and pWE/Ad.AflII-rITR (5 μg). Transfections were performed using 40 μl of Lipofectamine, and manufacturer instructions were followed. After overnight incubation at 37° C. in a 10% $CO_2$ atmosphere, the transfection medium was replaced with fresh DMEM with FBS 10% and $MgCl_2$ 10 mM. At 24, 48, 72 and 120 hours post-transfection, the PER.C6 cells were scraped, harvested and extrachromosomal DNA was isolated by the Hirt-extraction. The extracted DNA was digested for 1 hour at 37° C. with 20 units of Dpn I (Biolabs). The fragments were size separated on 0.3% high gel strength SeaKem gold agarose (FMC Bioproducts, Rockland Me., USA). DNA was Southern blotted (Maniatis et al., 1982) and hybridized with a LacZ $^{32}$p labeled DNA fragment (RTS labeling system, Gibco BRL, Life Technologies). The autoradiogram corresponding to this experiment (FIG. 10) clearly shows that, indeed, there is time dependency on the accumulation of Rfs mediated by AAV replication, being, three days post-transfection, the time-point where more replicated material is detected (lanes 3 and 8). It is important to mention the ability to detect replication of the Ad/AAV chimeric genome 33 Kb in size. The signal corresponding to the 33 Kb Ad/AAV replicated genome ranges from barely detectable at 48 hours post-transfection to fully visible at 72 and also 120 hours post-transfection. Once again, it is clearly observed the enhancement in the AAV-mediated replication provided by the presence of the E2A-containing expression plasmid (compare lane 2 with lane 4 and lane 7 with lane 10).

From the Ad/AAV production point of view, these results are particularly important since it should enable further maximization of Ad/AAV genome replication prior to infection, of transfected cells, with the helper ΔE1 adenoviral vector.

REFERENCES

1. Amalfitano A, Chamberlain J (1997). Isolation and characterization of packaging cell lines that coexpress the adenovirus E1, DNA polymerase and preterminal proteins: implications for gene therapy. Gene Ther 4: 258–263.
2. Balague C (1997). J. Virol 71: 3299–3306.
3. Berk A J (1986). Adenovirus promoters and E1A trans-activation. Ann. Rev. Genet. 20: 45–79.
4. Berns K, Bohensky R (1987). Adeno-associated virus: an update. Adv. Virus Res. 32: 243–306.
5. Berns K I (1990a). Parvoviridae and their replication. In: Virology, Raven Press, New York.
6. Berns K I (1990b). Parvovirus replication. Microbiol. Rev. 54: 316–329.
7. Blaese M, Blankenstein T, Brenner M, Cohen-Haguenauer 0, Gansbacher B, Russell S, Sorrentino B, Velu T (1995). Vectors in cancer therapy: how will they deliver? Cancer Gene Ther.2: 291–297.
8. Bout A, Imler J L, Schulz H, Perricaudet M, Zurcher C, Herbrink P, Valerio D, Pavirani A (1994a). In vivo adenovirus-mediated transfer of human CFTR cDNA to Rhesus monkey airway epithelium: efficacy, toxicity and safety. Gene Therapy 1: 385–394.
9. Bout A, Perricaudet M, Baskin G, Imler J L, Scholte B J, Pavirani A, Valerio D (1994b). Lung gene therapy: in vivo adenovirus mediated gene transfer to rhesus monkey airway epithelium. Human Gene Therapy 5: 3–10.
10. Brody S L, Crystal R G (1994). Adenovirus-mediated in vivo gene transfer. Ann N Y Acad Sci 716: 90–101.
11. Chejanovsky N. Carter B J (1989). Mutagenesis of an AUG codon in the adeno-associated virus rep gene: effects on viral DNA replication. Virology 173: 120–128.
12. Clark K, Voulgaropoulou F, Fraley D, Johnson P (1995). Cell lines for the production of recombinant adeno-associated virus. Human Gene Ther. 6: 1329–1341.
13. Clark K, Voulgaropoulou F, Johnson P (1996). A stable cell line carrying adenovirus-inducible rep and cap genes allows for infectivity titration of adeno-associated virus vectors. Gene Therapy 3: 1124–1132.
14. Einerhand M P, Antoniou M, Zolotukhin S, Muzyczka N, Berns K I, Grosveld F, Valerio D (1995). Regulated high-level human beta-globin gene expression in erythroid cells following recombinant adeno-associated virus-mediated gene transfer. Gene-Ther 2: 336–343.
15. Ellis J, Pasceri P, Tan Un K C, Wu X, Harper A, Fraser P, Grosveld F (1997). Evaluation of beta-globin gene therapy constructs in single copy transgenic mice. Nucleic-Acids-Res 25: 1296–302.
16. Ellis J, Tan Un K C, Harper A, Michalovich D, Yannoutsos N, Philipsen S, Grosveld F (1996). A dominant chromatin-opening activity in 5' hypersensitive site 3 of the human beta-globin locus control region. EMBO-J 15:562–8 issn: 0261–4189.
17. Engelhardt J F, Litzky L, Wilson J M (1994a). Prolonged transgene expression in cotton rat lung with recombinant adenoviruses defective in E2a. Hum. Gene Ther. 5: 1217–1229.
18. Engelhardt J F, Simon R H, Yang Y, Zepeda M, Weber-Pendleton S, Doranz B, Grossman M, Wilson J M (1993). Adenovirus-mediated transfer of the CFTR gene to lung of nonhuman primates: biological efficacy study. Human Gene Therapy 4: 759–769.
19. Engelhardt J F, Ye X, Doranz, B, Wilson J M (1994b). Ablation of E2A in recombinant adenoviruses improves transgene persistence and decreases inflammatory response in mouse liver. Proc Natl Acad Sci U S A 91: 6196–200.
20. Fallaux F J, Kranenburg O, Cramer S J, Houweling A, Ormondt Hv, Hoeben R C, Eb AJvd (1996). Characterization of 911: a new helper cell line for the titration and propagation of early-region-1-deleted adenoviral vectors. Hum. Gene Ther. 7: 215–222.
21. Ferrari F K, Samulski T, Shenk T, Samulski R J (1996). Second-strand synthesis is a rate-limiting step for efficient transduction by recombinant adeno-associated virus vectors. J-Virol 70: 3227–34 issn: 0022–538x.
22. Fiering S, Epner E. Robinson K, Zhuang Y. Telling A, Hu M, Martin D I, Enver T, Ley T J, Groudine M (1995). Targeted deletion of 5' HS2 of the murine beta-globin LCR reveals that it is not essential for proper regulation of the beta-globin focus. Genes-Dev 9: 2203–13 issn: 0890-9369.
23. Fortunati E, al. e (1996). In vitro and in vivo gene transfer to pulmonary cells mediated by cationic liposomes. Biochim. Biophys 1306: 55–62.
24. Graeble M, Hearing P (1990). Adenovirus type 5 packaging domain is composed of a repeated element that is functionally redundant. J Virol 64: 2047–2056.

25. Graeble M, Hearing P (1992). Cis and trans requirements for the selective packaging of adenovirus type 5 DNA. J Virol 66: 723–731.
26. Graham F L, Smiley J, Russell W C, Naiva R (1977). Characteristics of a human cell line transformed by DNA from adenovirus type 5. J. Gen. Virol. 36: 59–72.
27. Haddada H, Lopez M, Martinache C, Ragot T, Abina M A, Perricaudet M (1993). Efficient adenovirus-mediated gene transfer into human blood monocyte-derived macrophages. Biochem Biophys Res Commun 195: 1174–83.
28. Hearing P, Samulski R, Wishart W, Shenk T (1987). Identification of a repeated sequence element required for efficient encapsidation of the adenovirus type 5 chromosome. J Virol 61: 2555–2558.
29. Holscher C, Horer M, Kleinschmidt J A, Zentgraf H, Burkle A, Heilbronn R (1994). Cell lines inducibly expressing the adeno-associated virus (AAV) rep gene: Requirements for productive replication of rep negative AAV mutants. J of Virol 68: 7169–7177.
30. Jochemsen A G, Peltenburg L T C, Pas M F W T, Wit C Md, Bos J L, Eb AJvd (1987). EMBO J. 6: 3399–3405.
31. Johnston K M, Jacoby D, Pechan P A, Fraefel C, Borghesani P, Schuback D, Dunn R J, Smith F I, Breakefield X O (1997). HSV/AAV hybrid amplicon vectors extend transgene expression in human glioma cells. Hum-Gene-Ther 8: 359–70 issn: 1043–0342.
32. Kotin R M (1994). Prospects for the use of adeno-associated virus as a vector for human gene therapy. Hum-Gene-Ther 5: 1043–0342.
33. Kotin R M, Siniscalco M, Samulski R J, Zhu X, Hunter L, Laughlin S, Muzyczka N, Rocchi M, Berns K I (1990). Site-specific integration by adeno-associated virus. Proc Natl Acad Sci USA 87: 2211–2215.
34. Kruijer W, Nicolas J C, Schaik F Mv, Sussenbach J S (1983). Structure and function of DNA binding proteins from revertants of adenovirus type 5 mutants with a temperature-sensitive DNA replication. Virology 124: 425–433.
35. Lechner R L, Jr. T J K (1977). The structure of replicating adenovirus 2 DNA molecules. J. Mol. Biol. 174: 493–510.
36. Li Q, Stamatoyannopoulos G (1994). Hypersensitive site 5 of the human beta locus control region functions as a chromatin insulator. Blood 84: 1399–401 issn: 0006-4971.
37. Lusby E, Fife K H, Berns K I (1980). Nucleotide sequence of the inverted terminal repetition in adeno-associated virus DNA. J. Virol. 34: 402–409.
38. Maniatis T, Fritsch E F, Sambrook J (1982). Molecular cloning (A laboratory Manual). Cold Spring Harbor Laboratory Press, Cold Spring Harbor, N. Y.
39. Muzyczka N (1992). Use of adeno-associated virus as a general transduction vector for mammalian cells. Curr Top Microbiol Immunol 158: 97–129.
40. Nicolas J C, Suarez F, Levine A J, Girard M (1981). Temperature-independent revertants of adenovirus H5ts125 and H5ts107 mutants in the DNA binding protein: isolation of a new class of host range temperature conditional revertants. Virology 108: 521–524.
41. Parks R, Chen L, Anton M, Sankar U, Rudnicki M, Graham F (1996). A helper-dependent adenovirus vector system: Removal of helper virus by Cre-mediated excision of the viral packaging signal. Proc. Natl. Acad. Sci. USA 93: 13365–13570.
42. Parks R, Graham F (1997). A helper-dependent system for adenovirus vector production helps define a lower limit for efficient DNA packaging. J Virol 71: 3293–3298.
43. Roberts B E, Miller J S, Kimelman D, Cepko C L, Lemischka I R, Mulligan R C (1985). Individual Adenovirus Type 5 Early Region 1A Products Elicit Distinct Alterations of Cellular Morphology and Gene Expression. J. Virol. 56: 404–413.
44. Ruffing M, Heid H, Kleinschmidt J A (1994). Mutations in the carboxy terminus of adeno-associated virus 2 capsid proteins affect viral infectivity: lack of an RGD integrin-binding motif. J-Gen-Virol 75: 3385–92.
45. Samulski R J (1993). Adeno-associated virus. Integration at a specific chromosornal locus. Curr Opin Gen Dev 3: 74–80.
46. Samulski R J, Chang L, Shenk T (1989). Helper-free stocks of recombinant adeno-associated viruses: normal integration does not require viral gene expression. J. Virol. 63: 3822–3828.
47. Samulski R J, Zhu X, Xiao X, Brook J D, Housrnan D E, Epstein N, Hunter L A (1991). Targeted integration of adeno-associated virus (AAV) into human chromosome 19. EMBO J. 10: 3941–3950.
48. Schmid S, Hearing P (1997). Bipartite structure and functional independence of adenovirus type 5 packaging elements. J Virol 71: 3375–3384.
49. Simon R H, Engelhardt J F, Yang Y, Zepeda M, Weber-Pendleton S, Grossman M, Wilson J M (1993). Adenovirus-mediated transfer of the CFTR gene to lung of nonhuman primates: toxicity study. Human Gene Therapy 4: 771–780
50. Srivastava A, Lusby E, Berns K (1983). Nucleotide sequence and organization of the adeno-associated virus 2 genome. J. Virol. 45: 555–564.
51. Stratford-Perricaudet L, Perricaudet M (1991). Gene Transfer into Animals: the promise of adenovirus. In: Human gene transfer, INSERM.
52. Surosky R T, Urabe M, Godwin S G, McQuiston S A, Kurtzman G J, Ozawa K, Natsoulis G (1997). Adeno-associated virus Rep proteins target DNA sequences to a unique locus in the human genome. J-Virol 71: 7951–9.
53. Telling G C, Perera S, Szatkowski O M, Williams J (1994). Absence of an essential regulatory influence of the adenovirus E1 B 19-kilodalton protein on viral growth and early gene expression in human diploid W138, HeLa, and A549 cells. J Virol 68: 541–7.
54. Thrasher A, Alwis de M, Casimir C, Kinnon C, Lebkowski J, Segal A, Levinsky R (1995). Generation of recombinant adeno-associated virus (rAAV) from an adenoviral vector and functional reconstitution of the NADPH-oxidase. Gene Ther. 2: 481–485.
55. Tooze J (1961). DNA Tumor Viruses (revised). Cold Spring Harbor Laboratory, Cold Spring Harbor, New York.
56. Trempe J P, Carter B J (1988). Alternate mRNA splicing is required for synthesis of adeno-associated virus VP1 capsid protein. J of Virol 62: 3356–3363.
57. Tsukui T, Kanegae Y, Saito I, Toyoda Y (1996). Transgenesis by adenovirus-mediated gene transfer into mouse zona-free eggs. Nature Biotech 14: 982–985.
58. Vincent A J P E, Esandi Md C, Someren G Dv, Noteboom J L, C. J. J A, Vecht C, Smitt P A E S, Bekkum D Wv, Valerio D, Hoogerbrugge P M, Bout A (1996a). Treatment of Lepto-meningeal metastasis in a rat model using a recombinant adenovirus containing the HSV-tk gene. J. Neurosurg. 85: 648–654.
59. Vincent A J P E, Esandi Md C, Someren Gv, Noteboom J L, Avezaat C J J, Vecht C, Smitt PAES, Bekkum D Wv, Valerio D, Hoogerbrugge P M, Bout A (1996b). Recombinant adenoviral HSV-tk gene therapy for CNS malignancies. Neurosurg. submitted:

60. Vincent A J P E, Vogels R, Someren Gv, Esandi Md C, Noteboom J L, Avezaat C J J, Vecht C, Bckkum D Wv, Valerio D, Bout A, Hoogerbrugge P M (1996c). Herpes Simplex Virus Thymidine Kinase gene therapy for rat malignant brain tumors. Hum. Gene Ther. 7: 197–205.
61. Weitzman M D, Kyostio S R, Kotin R M, Owens P-A (1994). Adeno-associated virus (AAV) Rep proteins mediate complex formation between AAV DNA and its integration site in human DNA. Proc-Natl-Acad-Sci-U-S-A 91: 5808–12 issn: 0027-8424.
62. White F, Denton A, Stillman B (1988). J. Virol. 62: 3445–3454.
63. Yang Y, Li Q, Ertl H C J, Wilson J M (1995). Cellular and humoral immune responses to viral antigens create barriers to lung-directed gene therapy with recombinant adenoviruses. J. Virol. 69: 2004–2015.
64. Yang Y, Nunes F A, Berencsi K, Gonczol F, Engelhardt J F, Wilson J M (1994). Inactivation of E2a in recombinant adenoviruses improves the prospect for gene therapy in cystic fibrosis. Nat Genet 7: 362–9.
65. Zeng M, Cemiglia G, Eck S, Stevens C (1997). High-efficiency stable gene transfer of adenovirus into mammalian cells using ionizing radiation. Hum Gene,Ther 8: 1025–1032.

TABLE 1

Functional LacZ-activity following cloning of a PCR-product containing a CMV-LacZ expression cassette.

| Construct | % blue cells |
|---|---|
| pAdyLacZ | 50% |
| pAdTR y LacZ | 90% |
| pD18AdTR y LacZ | 70% |
| Positive control[a] | 40% |
| Negative control | 0% |

[a]Positive control is a non-related LacZ-construct previously shown to be functional.

TABLE 2

Number of LacZ positive HeLa cells upon infection with minimal Ad/AAV chimeric virus particles.

| | Virus produced in absence of Rep[ξ] | | Virus produced in the presence of Rep[ξ] | |
|---|---|---|---|---|
| CONSTRUCT | 1/20 Virus Dilution | 1/4 Virus Dilution | 1/20 Virus Dilution | 1/4 Virus Dilution |
| pTR-AdyLacZ | 1 | 1 | 3 | 11 |
| pTR-DI8AdTRyLacZ | 0 | 0 | 15 | 29 |

TABLE 2-continued

Number of LacZ positive HeLa cells upon infection with minimal Ad/AAV chimeric virus particles.

| | Virus produced in absence of Rep[ξ] | | Virus produced in the presence of Rep[ξ] | |
|---|---|---|---|---|
| CONSTRUCT | 1/20 Virus Dilution | 1/4 Virus Dilution | 1/20 Virus Dilution | 1/4 Virus Dilution |
| pTR-AdTRyLacZ | 0 | 0 | 14 | 101 |
| pTR-AdTRyLacZ[φ] | 0 | 0 | 0 | 4 |

[ξ]Number of blue cells detected after X-Gal staining of chimeric virus infected HeLa cells.
[φ]Is the same as pTR-AdTRyLacZ, however, both AAV-TR have undergone rearrangement during the cloning process in bacteria as judged by aberrant AhdI and Bg/I-digestion patterns. AAV-rep mediated replication of this construct in adenovirus infected PER.C6 cells is severely impaired (FIG. 4).

TABLE 3

β-Gal and Luciferase assays after CsCl block gradient of 13.8 Kb Ad/AAV chimeric vector production

| Fraction Number | RLU* | BFU/10 μl | Titer (BFU/ml) |
|---|---|---|---|
| 10 | 7186 | 0 | — |
| 11 | 9511 | 0 | — |
| 12 | 164697 | 215 | $2, 2 \times 10^4$ |
| 13 | 437864 | 49 | $0, 5 \times 10^4$ |
| 14 | 50561 | 0 | — |
| 15 | 31955 | 0 | — |
| (−) | 143 | 0 | — |

RLU* - Relative Luciferase Units
(−) - Negative sample corresponding to uninfected HeLa cells

TABLE 4

β-Gal. and Luciferase assays of the 13.8 Kb Ad/AAV chimeric vector CsCl block gradient-containing fractions after CsCl continuous gradient and Centricon-100 CsCl desalting.

| Fraction Number | RLU* | BFU/20 μl | Titer (BFU/ml) |
|---|---|---|---|
| 6 | 15385 | 0 | — |
| 7 | 18319 | 97 | $0, 5 \times 10^4$ |
| 8 | 972 | 12 | $0, 6 \times 10^3$ |
| 9 | 360 | 0 | — |
| 10 | 353 | 0 | — |
| 11 | 201 | 0 | — |
| 12 | 160 | 0 | — |
| (−) | 53 | 0 | — |

RLU* - Relative Luciferase Units
(−) - Negative sample corresponding to uninfected HeLa cells

What is claimed is:

1. A chimeric replication-defective adenoviral vector comprising:
   a functional packaging signal sequence derived from an adenovirus;
   a nucleic acid sequence of interest directly linked to the functional packaging signal sequence;
   a first AAV-ITR linked to the functional packaging signal sequence opposite the nucleic acid sequence of interest; and
   a second AAV-ITR directly linked to the nucleic acid sequence of interest opposite the functional packaging signal sequence.

2. The chimeric replication-defective adenoviral vector of claim 1, wherein the adenovirus from which the functional packaging signal sequence is derived is capable of efficiently infecting a host.

3. The chimeric replication-defective adenoviral vector of claim 1, further comprising a trans-acting sequence encoding a functional adeno associated virus rep gene.

4. The chimeric replication-defective adenoviral vector of claim 1, wherein the nucleic acid sequence of interest comprises one or more genes.

5. The chimeric replication-defective adenoviral vector of claim 1, wherein the nucleic acid sequence of interest encodes an antisense sequence.

6. The chimeric replication-defective adenoviral vector of claim 1, further comprising regulatory elements for expressing the nucleic acid sequence of interest.

7. The chimeric replication-defective adenoviral vector of claim 1, further comprising a suicide gene.

8. A replication-defective adenoviral particle comprising the chimeric replication-defective adenoviral vector of claim 1.

9. An in vitro cell comprising the chimeric replication-defective adenoviral vector of claim 1.

10. A method for producing a replication-defective adenoviral particle comprising a chimeric replication-defective adenoviral vector, the method comprising:
    providing a cell with a chimeric replication-defective adenoviral vector comprising:
        a functional packaging signal sequence derived from an adenovirus;
        a nucleic acid sequence of interest directly linked to said functional packaging signal sequence;
        a first AAV-ITR linked to said functional packaging signal sequence opposite said nucleic acid sequence of interest; and
        a second AAV-ITR directly linked to said nucleic acid sequence of interest opposite said functional packaging signal sequence; and
    providing said cell with elements necessary for producing said replication-defective adenoviral particle, said elements comprising a trans-acting sequence encoding a functional adeno associated virus rep gene.

11. The method according to claim 10, wherein a first element of said elements necessary for production of said replication-defective adenoviral particle is present in said chimeric replication-defective adenoviral vector and a second element of said elements necessary for production of said replication-defective adenoviral particle is present in an adenoviral packaging vector present in said cell.

12. The method according to claim 10, wherein said elements necessary for production of said adenoviral particle are present on an adenoviral packaging vector present in said cell.

13. A packaging cell comprising genetic elements for producing a replication-defective adenoviral particle, the genetic elements comprising a functional packaging signal sequence derived from an adenovirus, a nucleic acid sequence of interest directly linked to said functional packaging signal sequence, a first AAV-ITR linked to said functional packaging signal sequence opposite said nucleic acid sequence of interest, and a second AAV-ITR directly linked to said nucleic acid sequence of interest opposite said functional packaging signal sequence.

14. An rAAV nucleic acid comprising:
    a functional packaging signal sequence derived from an adenovirus;
    a nucleic acid sequence larger than 6.5 kb directly linked with said functional packaging signal sequence;
    a first ITR directly linked with said nucleic acid sequence opposite said functional packaging signal sequence; and
    a second ITR linked to said functional packaging signal sequence opposite said nucleic acid sequence, each of said first and second ITRs comprising an ITR selected from a group consisting of an AAV-ITR and a functional portion of an AAV-ITR necessary for AAV replication.

* * * * *

UNITED STATES PATENT AND TRADEMARK OFFICE
CERTIFICATE OF CORRECTION

PATENT NO.     : 6,468,771 B1
DATED          : October 22, 2002
INVENTOR(S)    : Markus Peter Einerhand, Domenico Valerio and Govert Johan Schouten It is certified that error appears in the above-identified patent and that said Letters Patent is hereby corrected as shown below:

Title page,
Item [57], ABSTRACT,
Line 6, after "integration" and before "derived" insert -- means --
Line 9, after "recombinant" change "process" to -- means --

Column 4,
Line 53, delete the period after "as"
Line 66, change "arc" to -- are --

Column 6,
Line 55, change "been-identified" to -- been identified --

Column 15,
Lines 42-43, change "the-invention" to -- the invention --

Column 16,
Line 33, change "TR-AdTRyLacZ" to -- pTR- AdTRyLacZ --

Column 17,
Lines 48 and 60, change "NsiI-site" to -- NsiI-site --

Column 19,
Line 40, change "SK$^-$" to -- SK$^+$ --

Column 20,
Line 15, change "S" to -- 5 --
Line 26, change "DH5a" to -- DH5α --
Line 60, change "Pact" to -- PacI --

Column 21,
Line 12, change "˜150" to -- ~150 --

Column 22,
Line 31, change "DH5a" to -- DH5α --

Column 23,
Line 61, change "molecules-of" to -- molecules of --

UNITED STATES PATENT AND TRADEMARK OFFICE
CERTIFICATE OF CORRECTION

PATENT NO. : 6,468,771 B1
DATED : October 22, 2002
INVENTOR(S) : Markus Peter Einerhand, Domenico Valerio and Govert Johan Schouten It is certified that error appears in the above-identified patent and that said Letters Patent is hereby corrected as shown below:

<u>Column 24,</u>
Line 63, change "an d" to -- and --

<u>Column 25,</u>
Line 54, delete the period after "the"

<u>Column 26,</u>
Line 16, change "P-Gal" to -- β-gal --

<u>Column 27,</u>
Line 13, change "cTr$^+$LacZ," to -- cTR$^+$LacZ, --
Line 26, delete the period after "and"

<u>Column 33,</u>
Line 2, change "Bckkum" to -- Bekkum --
Line 21, change "Cemiglia" to -- Cerniglia --
Line 55, change "pTR-DI8AdTRyLacZ" to -- pTR-D18AdTRyLacZ --

Signed and Sealed this

Seventeenth Day of June, 2003

JAMES E. ROGAN
*Director of the United States Patent and Trademark Office*